(12) United States Patent
Mandrand et al.

(10) Patent No.: US 7,446,186 B2
(45) Date of Patent: Nov. 4, 2008

(54) PYRROLES SUBSTITUTED BY OLIGONUCLEOTIDES

(75) Inventors: Bernard Mandrand, Villeurbanne (FR); Daniela Zsoldos, Noyarey (FR); Alain Laurent, Grenoble (FR); Carole Chaix, Chapponnay (FR); Nicolas Spinelli, Lyons (FR)

(73) Assignee: Biomerieux, Marcy l'Etoile (FR)

( * ) Notice: Subject to any disclaimer, the term of this patent is extended or adjusted under 35 U.S.C. 154(b) by 389 days.

(21) Appl. No.: 10/536,317

(22) PCT Filed: Dec. 16, 2003

(86) PCT No.: PCT/FR03/03747

§ 371 (c)(1),
(2), (4) Date: Jul. 26, 2005

(87) PCT Pub. No.: WO2004/060904

PCT Pub. Date: Jul. 22, 2004

(65) Prior Publication Data

US 2006/0189555 A1    Aug. 24, 2006

(30) Foreign Application Priority Data

Dec. 19, 2002    (FR) .................................. 02/16184

(51) Int. Cl.
*C07H 21/00*    (2006.01)
*C12Q 1/68*    (2006.01)

(52) U.S. Cl. .................. 536/23.1; 536/25.3; 435/6

(58) Field of Classification Search ............... 536/23.1, 536/25.3; 435/6
See application file for complete search history.

(56) References Cited

U.S. PATENT DOCUMENTS 6,197,949 B1    3/2001    Teoule et al.

FOREIGN PATENT DOCUMENTS

| EP | 0 691 978 B1 | 1/1996 |
|---|---|---|
| EP | 0 912 593 B1 | 5/1999 |
| FR | 2 607 507 | 6/1988 |
| WO | WO 91/06625 A1 | 5/1991 |

(Continued)

OTHER PUBLICATIONS

Kocienshi, "Protecting Groups," Thine Publishing Group, 1994.

(Continued)

*Primary Examiner*—Jezia Riley
(74) *Attorney, Agent, or Firm*—Oliff & Berridge, PLC

(57) ABSTRACT

The invention relates to novel pyrrole derivatives of the formula (I) which make it possible to immobilize and address oligonucleotides by electropolymerization. Said invention also relates to thus produced electroactive polymers and to methods for using them for detecting, identifying and dosing analytes in a sample. (I) wherein $R_1$ is one type of oligonucleotide, Y is S or O, X is a spacer arm selected from —$(CH_2)$—O—, —$(CH_2)<SB>P</SB>O$—[$(CH_2)_2$—O]$_q$—, —$(CH2)_r$; —CO—NR'—$(CH_2)_{r'}$—O—, —$CH_{2r}$—$NCH_3$—$(CH_2)_{r'}$—O—, —$(CH_2)_r$CO—NR'—[$(CH_2)_2$—O]$_s$—, —$(CH_2)_r$$NCH_3$[$(CH_2)_2$—O]<SB>S</SB>—, R' is H or $CH_3$, n is an integer number ranging from 1 to 5, p is an integer number ranging from 1 to 2, q is an integer number ranging from 1 to 4, r is an integer number ranging from 1 to 3, r' is an integer number ranging from 1 to 3, s is an integer number ranging from 1 to 3, n, p, q, r, r' and s are identical or different, a pyrrole cycle is substituted in a position 2, 3, 4 or 5.

21 Claims, 10 Drawing Sheets

FOREIGN PATENT DOCUMENTS

| WO | WO 94/22889 A1 | 10/1994 |
| --- | --- | --- |
| WO | WO 95/29199 A1 | 11/1995 |
| WO | WO 97/22648 A1 | 6/1997 |
| WO | WO 97/49718 A1 | 12/1997 |
| WO | WO 00/77523 A1 | 12/2000 |

OTHER PUBLICATIONS

Greene et al., "Protective Groups In Organic Synthesis," *Continuum International Publishing Group*, Second Edition, 1991.

Sadki et al., "The Mechanisms of Pyrrole Electropolymerization," *Chem. Soc. Rev.*, vol. 29, pp. 283-293, 2000.

Egholm et al., "Peptide Nucleic Acids (PNA). Oligonucleotide Analogues with an Achiral Peptide Backbone," *American Chemical Society*, Vo. 114, pp. 1895-1897.

Lassalle et al., "Electropolymerisable pyrrole-oligonucleotide: synthesis and analysis of ODN hybridization by fluorescence and QCM," Talanta, vol. 55, pp. 993-1004, 2001.

Settambolo et al., Rhodium-Catalyzed Hydroformylation of 2-vinyl—and 3-vinyl-1-tosylpyrroles as a Convenient Synthetic Route to the Corresponding 2-(1-tosylpyrrolyl) propanals and Derivatives, Synthetic Communications, vol. 27, No. 23, pp. 4111-4120, 1997.

Ho-Hoang et al., Synthesis and Characterization of Organic Conductors Derived from (1$H$-pyrrol-3-yl) Acetic Acid Esters, J. Mater, Chem., vol. 6, No. 7, pp. 1107-1112, 1996.

Ho-Hoang et al., "Synthesis and Electrochemical Characterization of Functionalized 3-Substituted Polypyrroles," Synthetic Metals, vol. 62, pp. 277-280, 1994.

Garnier et al., "Toward Intelligent Polymers: DNA Sensors Based on Oligonucleotide-Functionalized Polypyrroles," Synthetic Metals, vol. 100, pp. 89-94, 1999.

Livache et al., "Polypyrrole DNA Chip on a Silicon Device: Example of Hepatitis C Virus Genotyping," Analytical Biochemistry, vol. 255, No. AB972462, pp. 188-194, 1998.

Garnier et al., "Enzyme Recognition by Polypyrrole Functionalized with Bioactive Peptides," J. Am. Chem., vol. 116, pp. 8813-8814, 1994.

Korri-Youssoufi et al., "Synthesis of 3-derivatized Pyrroles Precursors Polymers for Functionalization with Biomolecules Toward Biosensor Devices," Materials Science and Engineering C, vol. 15, pp. 265-268, 2001.

Korri-Youssoufi et al, "Electrochemical Biosensing of DNA Hybridization by Electroactive Ferrocene Functionalized Polypyrrole," Synthetic Metals, vol. 119, pp. 265-266, 2001.

PYRROLES SUBSTITUTED BY OLIGONUCLEOTIDES

The present invention relates to novel pyrrole derivatives for the immobilization and targeting of oligonucleotides by electropolymerization. The invention also relates to the electroactive polymers thus obtained, and to methods for using them for detecting, identifying and assaying analytes in a sample.

Conjugated polymers, such as polypyrroles and their derivatives, are well known for their conductive and electroactive nature. It is also known that polypyrroles conserve their conductivity and their electro-activity when certain pyrrole rings are substituted in the 3- or 4-position with functional groups. Polymers carrying functional groups of this type are described in WO-A1-95/29199, Garnier et al. (*Synthetic Metals*, 100: 89-94, 1999) Ho-Hoang et al. (*Synthetic Metals*, 62: 277-280, 1994), Ho-Hoang et al. (*J. Mater. Chem.*, 6(7), 1107-1112, 1996), and Korri-Youssoufi et al. (*Materials Science and Engineering*, C15, 265-268, 2001). Different antiligands can then be grafted onto the functional groups carried by the polypyrroles.

Thus, WO-A1-95/29199 describes the synthesis of a precursor polypyrrole by means of the electrochemical polymerization of pyrroles substituted in the 3-position of the pyrrole ring with functional groups. This precursor polymer is deposited, by electrochemical polymerization, onto a conductive substrate or in the form of a self-supporting film. In a second step, an antiligand such as a polynucleotide or a peptide is chemically grafted onto the functional groups of the precursor polymer. The polymer thus obtained conserves its conductive and electroactive properties. These polymers can therefore be used for detecting an analyte that interacts specifically with the antiligand grafted onto the polymer, by measuring a potential difference or a current variation. WO-A1-00/77523 also describes the chemical grafting of an antiligand, such as an oligonucleotide, onto a precursor polymer carrying functional groups.

The polymers thus obtained can be used as biological sensors or "biosensors" for capturing and detecting an analyte. The possibility of detecting an analyte, such as a molecule of biological interest, in a sample by means of a simple electrical measurement constitutes the main advantage of these polymers. However, the methods for preparing these polymers involve chemical grafting that does not allow the synthesis, in parallel, of a large number of polymers carrying different antiligands. Now, the preparation of antiligand matrices requires the immobilization and targeting of a large number of different antiligands. The production of "biochips" or DNA chips thus involves the immobilization and targeting of oligonucleotide matrices on solid supports. The methods for chemical grafting of oligonucleotides onto a precursor polymer do not make it possible to obtained ordered matrices of oligonucleotides.

Moreover, it is known practice to perform the targeting and the immobilization of oligonucleotides simultaneously by direct electrochemical copolymerization of a mixture of unsubstituted pyrroles and of pyrroles substituted on the nitrogen atom with a group carrying an oligonucleotide. Livache et al. (*Analytical Biochemistry*, 255: 188-194, 1998) thus describe the synthesis of substituted pyrroles in which a group carrying an oligonucleotide is substituted on the nitrogen atom of the pyrrole ring. These substituted pyrroles carrying an oligonucleotide are electrochemically copolymerized with pyrrole. Successive electrochemical copolymerization reactions allow the targeting and the immobilization of different oligonucleotide matrices on different electrodes. By means of electropolymerization, copolymers carrying oligonucleotides that can be used for hybridization reactions for detecting specific DNAs or RNAs are obtained. However, these copolymers have weak conductive and electroactive properties. The drawback of these polymers is therefore that the detection of the hybridization is carried out by means of additional labeling, and not by means of a direct electrical measurement.

EP-B1-0 691 978 and EP-B1-0912 593 also describe substituted pyrroles onto which various ligands, such as oligonucleotides, are grafted on the nitrogen of the pyrrole ring. These substituted pyrroles, used as monomers, are electrochemically copolymerized with unsubstituted pyrrole. However, the copolymers obtained also have the drawback of having weak conductive and electroactive properties.

In order to remedy the drawbacks of the state of the art, the present invention proposes novel pyrroles that are substituted elsewhere than on the nitrogen atom, with groups carrying oligonucleotides. These novel substituted pyrroles allow the synthesis of copolymers by electrochemical polymerization when they are used as monomers, alone or as a mixture with other monomers. The polymers or copolymers obtained are conductive and electroactive. The pyrroles substituted with oligonulceotides according to the invention offer the possibility of targeting and immobilizing oligonucleotides by electrochemical polymerization, in a single step. The pyrroles substituted with oligonucleotides and the copolymers according to the invention therefore make it possible to prepare ordered matrices of oligonucleotides. These matrices constitute particularly advantageous tools for diagnosis and for the screening of molecules in series. In addition, the copolymers according to the invention have electroactive properties for detecting, by means of an electrical measurement, an analyte capable of interacting specifically with the oligonucleotides carried by the copolymer.

DESCRIPTION OF THE INVENTION

The present invention relates to pyrroles substituted with groups carrying an oligonucleotide. These substituted pyrroles according to the invention are hereinafter defined as "pyrrole substituted with an oligonucleotide" or "substituted pyrrole according to the invention".

A first subject of the present invention is a pyrrole substituted with an oligonucleotide, characterized in that it corresponds to general formula (I):

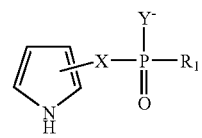

in which
$R_1$ represents an oligonucleotide,
Y represents S or O,
X represents a spacer arm.

The term "spacer arm" is intended to mean a chemical group that makes it possible to distance the oligonucleotide with respect to the pyrrole ring. Spacer arms are well known to those skilled in the art, any spacer arm that makes it possible to conserve the conductive and electroactive properties of the polymer can be used in the substituted pyrroles according to the invention. Advantageously, the spacer arm represents a low hindrance so as not to interfere with the polymerization of the substituted pyrrole.

In a preferred embodiment of the invention, X represents a spacer arm chosen from —$(CH_2)_n$—O—, —$(CH_2)_p$—O—[$(CH_2)_2$—O]$_q$—, —$(CH_2)_r$—CO—NR'—$(CH_2)_r$—O—, —$(CH_2)_r$—NCH$_3$—$(CH_2)_r$—O—, —$(CH_2)_r$—CO—NR' [$(CH_2)_2$—O]$_s$—, —$(CH_2)_r$—NCH$_3$—[$(CH_2)_2$—O]$_s$—, R' represents —H or —CH$_3$, n is an integer between 1 and 5, p is an integer between 1 and 2, q is an integer between 1 and 4, r is an integer between 1 and 3, r' is an integer between 1 and 3, s is an integer between 1 and 3, n, p, q, r, r' and s are identical or different, the pyrrole ring is substituted in the 2-, 3-, 4- or 5-position.

The term "oligonucleotide" denotes a series of at least 2 natural or modified nucleotides (deoxyribonucleotides or ribonucleotides, or both) capable of hybridizing, under appropriate hybridization conditions, with an at least partially complementary oligonucleotide. The term "nucleoside" is intended to mean an organic compound consisting of a purine or pyrimidine base linked to a monosaccharide (ribose or deoxyribose). The term "nucleotide" is intended to mean an organic compound consisting of a purine or pyrimidine base linked to a monosaccharide (ribose or deoxyribose) and to a phosphate group. The term "modified nucleotide" is intended to mean, for example, a nucleotide comprising a modified base and/or comprising a modification to the internucleotide linkage and/or to the backbone. By way of example of a modified base, mention may be made of inosine, methyl-5-deoxycytidine, dimethylamino-5-deoxy-uridine, diamino-2,6-purine and bromo-5-deoxyuridine. To illustrate a modified internucleotide linkage, mention may be made of phosphorothioate, N-alkyl-phosphoramidate, alkylphosphonate and alkylphosphotriester linkages. Alpha-oligonucleotides such as those described in FR-A-2 607 507 and the PNAs that are the subject of the article by M. Egholm et al. (*J. Am. Chem. Soc.*, 114, 1895-1897, 1992) are examples of oligonucleotides consisting of nucleotides whose backbone is modified.

The oligonucleotide is linked to the spacer arm via a phosphodiester linkage. More specifically, the 3'-OH or the 5'-OH of the oligonucleotide is linked to the oxygen atom of the spacer arm by means of a phosphorylated group. Advantageously, the oligonucleotide comprises 2-70 nucleotides, preferably 20 nucleotides.

In an advantageous embodiment of the invention, the oligonucleotide comprises, at the end linked to the spacer arm, a polynucleotide of sequence TTTTT comprising from 5 to 10 T, preferably 10 T. This polyT makes it possible to distance the part of the oligonucleotide that is specific to the analyte to be detected, from the pyrrole ring.

The present invention also relates to a pyrrole substituted with an oligonucleotide of formula (II):

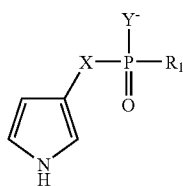

in which $R_1$, Y and X are as defined above.

Preferably, X is —$(CH_2)_n$—O— and n is equal to 2.

The present invention also relates to a pyrrole substituted with an oligonucleotide of general formula (III):

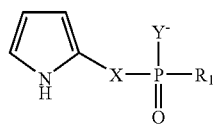

in which $R_1$, Y and X are as defined above.

Preferably, X is —$(CH_2)_n$—O— and n is equal to 2.

Another subject of the present invention consists of methods for preparing a conductive electroactive copolymer functionalized with oligonucleotides, comprising the following steps:

a) at least one monomer chosen from the pyrroles substituted with an oligonucleotide according to the invention of general formula (II) is provided, b) at least one monomer chosen from the substituted pyrroles capable of copolymerizing with other pyrroles is provided, c) the monomer of step a) is electrochemically copolymerized with the monomer of step b).

Advantageously, X is —$(CH_2)_n$—O— and n is equal to 2 in the pyrrole substituted with an oligonucleotide of general formula (II).

In another advantageous embodiment, the molar ratio of the pyrrole substituted with an oligonucleotide of general formula (II) according to the invention to the substituted pyrrole of step b) is 1/1000 to 1/100 000. Preferably, this molar ratio is from 1/5000 to 1/20 000. Even more preferably, this molar ratio is 1/20 000.

The term "monomer" is intended to mean a chemical unit capable of a chemical or electrochemical polymerization reaction with other monomers so as to form a polymer.

The term "polymerization" is intended to mean a chemical or electrochemical reaction of units of the same chemical nature, allowing the assembly of a certain number of monomers so as to form a macro-molecule (n×M→(M)$_n$). It typically involves the condensation of pyrrole units so as to form polypyrrole. The term "copolymerization" is intended to mean the simultaneous polymerization of different units, for instance the simultaneous polymerization of a mixture of pyrroles substituted with groups not containing oligonucleotides and of substituted pyrroles according to the invention.

The terms "electropolymerization", "electrocopolymerization", "electrochemical copolymerization" and "electrochemical polymerization" denote a polymerization by means of an electrochemical process. The electropolymerization methods are well known to those skilled in the art. Mention will, for example, be made of the techniques of cyclic voltammetry, chronopotentiometry (imposed current) and chronoamperometry (imposed potential). In a particular embodiment of the invention, the deposits are carried out by chronoamperometry or controlled potential deposition. This method consists in imposing a surge in potential from the equilibrium potential (zero current) to a fixed value at which the reaction takes place at the electrode, and in measuring the current as a function of time.

Electropolymerization of pyrrole by the Diaz mechanism (Sadki et al., *Chem. Soc. Rev.*, 29: 283-293, 2000) results in the formation of polypyrrole. This polymerization is carried out at the 2- and 5-positions of the pyrrole monomers.

The expression "substituted pyrrole capable of polymerizing with other pyrroles" is intended to mean a pyrrole substituted in the 3- or 4-position of the pyrrole ring that is capable of polymerizing or of copolymerizing with other pyrroles at the 2- and 5-positions, and more particularly of copolymerizing with pyrroles substituted with oligonucleotides according to the invention. These substituted pyrroles, capable of polymerizing with other pyrroles, carry groups that represent a molecular hindrance sufficiently small so as not to interfere in a polymerization or copolymerization reaction. Typically, these substituted pyrroles do not carry substituent groups containing oligonucleotides. Moreover, these pyrroles substituted in the 3- or 4-position of the pyrrole ring with low hindrance groups make it possible, after polymerization or copolymerization with other pyrroles, to obtain conductive and electroactive polymers. Substituted pyrroles capable of polymerizing with other pyrroles so as to form conductive polymers are well known to those skilled in the art and widely described in the literature. Mention will in particular be made of WO-A1-95/29199, Garnier et al. (*Synthetic Metals*, 100: 89-94, 1999), Ho-Hoang et al. (*Synthetic Metals*, 62: 277-280, 1994), Ho-Hoang et al. (*J. Mater. Chem.*, 6(7), 1107-1112, 1996), and Korri-Youssoufi et al. (*Materials Science and Engineering*, C15, 265-268, 2001). The copolymerization of pyrroles substituted with an oligonucleotide according to the invention with pyrroles substituted with groups that do not carry oligonucleotides makes it possible to decrease the hindrance during the copolymerization reaction.

Thus, when the pyrroles substituted with an oligonucleotide of the present invention are substituted in the 3- and 4-position of the pyrrole ring, a mixture of these pyrroles according to the invention with substituted pyrroles can be directly copolymerized.

In an advantageous embodiment of the invention, the pyrroles substituted with an oligonucleotide (ODN) according to the invention are copolymerized with 3-(hydroxyethyl)pyrrole. In this embodiment, the substituted pyrrole capable of polymerizing with other pyrroles is therefore 3-(hydroxyethyl)pyrrole. The conductive electroactive copolymer functionalized with oligonucleotides resulting from this copolymerization is represented below.

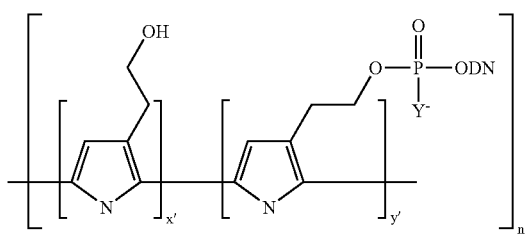

In particular embodiments of the invention, the copolymer functionalized with oligonucleotides is deposited or formed on a first conductive and electroactive polymer. In these methods, a first substituted pyrrole is polymerized or copolymerized so as to form a prefilm or a thin sublayer of conductive and electroactive polymer. Next, a second layer is produced with the copolymer functionalized with oligonucleotides.

The present invention therefore also relates to a method for preparing a conductive electroactive copolymer functionalized with oligonucleotides, comprising the following steps:
a) at least one monomer chosen from the substituted pyrroles capable of polymerizing with other pyrroles is provided,
b) this monomer of step a) is electrochemically polymerized so as to form a first conductive electroactive polymer,
c) a monomer chosen from the pyrroles substituted with an oligonucleotide of general formula (II) is provided,
d) at least one monomer chosen from the substituted pyrroles capable of polymerizing with other pyrroles is provided,
e) the monomer of step c) is electrochemically copolymerized with the monomer of step d) on said first conductive electroactive polymer formed in step b), so as to obtain a conductive electroactive copolymer functionalized with oligonucleotides.

The substituted pyrroles used in step a) and in step d) are identical or different.

Preferably, the molar ratio of the substituted pyrrole of step c) to the substituted pyrrole of step d) is 1/20 000.

Advantageously, the substituted pyrrole of step a) and of step d) is 3-(hydroxyethyl)pyrrole.

The invention also relates to a method for preparing a conductive electroactive copolymer functionalized with oligonucleotides, comprising the following steps:
a) at least one monomer chosen from the substituted pyrroles capable of polymerizing with other pyrroles is provided,
b) this monomer of step a) is electrochemically polymerized so as to form a first conductive electroactive polymer,
c) a monomer chosen from the pyrroles substituted with an oligonucleotide of general formula (II) is provided,
d) the monomer of step c) is electrochemically polymerized on said first conductive electroactive polymer formed in step b), so as to obtain a conductive electroactive polymer functionalized with oligonucleotides.

Advantageously, the substituted pyrrole of step a) is 3-(hydroxyethyl)pyrrole.

The present invention also relates to a method for preparing a conductive electroactive copolymer functionalized with oligonucleotides, comprising the following steps:
a) at least one monomer chosen from the substituted pyrroles capable of polymerizing with other pyrroles is provided,
b) this monomer of step a) is electrochemically polymerized so as to form a first conductive electroactive polymer,
c) a pyrrole substituted with an oligonucleotide according to general formula (III) is provided,
d) the substituted pyrrole of step c) is electrochemically coupled on the first conductive electroactive polymer formed in step b), so as to obtain a conductive electroactive copolymer functionalized with oligonucleotides.

Advantageously, the substituted pyrrole of step a) is 3-(hydroxyethyl)pyrrole.

When the pyrrole substituted with an oligonucleotide according to the invention is substituted in the 2- or 5-position of the pyrrole ring, it is not capable of polymerizing or of copolymerizing with other pyrroles. To prepare a conductive electroactive copolymer functionalized with oligonucleotides from pyrroles substituted with an oligonucleotide of general formula (III), it is therefore necessary to prepare a first conductive electroactive polymer on which the pyrrole substituted with an oligonucleotide in the 2- or 5-position according to the invention is electrochemically coupled.

In an advantageous embodiment of the invention, the pyrroles substituted with an oligonucleotide (ODN) of general formula (III) are therefore electrochemically coupled on a first conductive electroactive polymer of poly[3-(hydroxyethyl)pyrrole]. In this embodiment, the pyrrole substituted with an oligonucleotide according to the invention is therefore at the end of the polymeric chain. The conductive electroactive copolymer functionalized with oligonucleotides resulting from this copolymerization is represented below.

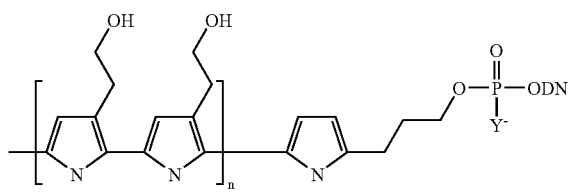

Another subject of the present invention consists of conductive electroactive copolymers functionalized with oligonucleotides that can be obtained by means of a method according to the invention.

The copolymers according to the invention are functionalized with oligonucleotides. These oligonucleotides are covalently grafted onto certain monomer units (pyrrole rings) forming the polymer, thus providing these conductive electroactive polymers with an additional function. The copolymers functionalized with oligonucleotides are, for example, suitable for capturing and detecting analytes.

The term "conductive polymer" is intended to mean a polymer whose electrons are highly delocalized, most commonly along a chain of single and double bonds (conjugated bonds), which leads it to behave like a microelectronic semiconductor.

The term "electroactive polymer" is intended to mean a polymer whose electrochemical response is modified when an analyte interacts specifically with the oligonucleotides carried by the polymer. Thus, a modification of the electrochemical signal is observed following the specific interaction with the analyte. The conductive electroactive copolymer therefore translates the interaction with the analyte into a modified electrochemical signal.

The copolymers according to the invention can be used in any of the applications in which oligonucleotides are targeted onto and immobilized on a solid support.

More particularly, the polymers according to the invention are obtained in the form of self-supporting films or in the form of a film on an electrode. The electrode in fact makes it possible to control, by measuring the current delivered during the reaction, the evolution of the polymerization reaction. The electrode also makes it possible to measure the subsequent electrochemical responses of the copolymer. The present invention therefore also relates to an electrode comprising a conductive support surface-coated with at least one conductive electroactive copolymer functionalized with oligonucleotides according to the invention.

Conductive supports for electrodes are known from the state of the art; mention will in particular be made of substrates made of metal or of carbon derivatives. For the production of an electrode according to the invention, the copolymer is generally deposited onto the conductive support. The electrochemical copolymerization is advantageously carried out at the surface of the electrode, so as to obtain an electrode comprising a conductive support surface-coated with a copolymer according to the invention. In an advantageous embodiment of the invention, the electrode is obtained by depositing a layer of copolymer at the surface of a support made of gold or of platinum.

Given that it is possible to limit and to control the electrochemical polymerization reactions at an electrode, the pyrroles substituted with an oligonucleotide according to the present invention make it possible to immobilize and to target oligonucleotides on small surfaces. This targeted electrocopolymerization makes it possible to produce a matrix of miniaturized and ordered points, each of the points carrying a defined oligonucleotide. In an advantageous embodiment, the invention therefore also relates to a matrix of electrodes.

The invention therefore also relates to a matrix of electrodes comprising at least one electrode according to the invention. In an advantageous embodiment, the various electrodes of the matrix carry different oligonucleotides. According to a particular embodiment, the invention relates to a plurality of electrodes or of microelectrodes attached to a solid support, these electrodes being coated with a copolymer according to the invention and advantageously carrying different oligonucleotides. Such electrode matrices can advantageously be obtained by targeted electropolymerization of pyrroles substituted with an oligonucleotide according to the invention.

The copolymers, the electrodes and the electrode matrices according to the invention can in particular be used for detecting analytes that may be present in a sample and that are capable of reacting specifically with the oligonucleotides carried by the copolymer. The invention therefore also relates to devices for detecting an analyte in a sample, comprising at least one copolymer according to the invention and/or at least one electrode according to the invention. The invention also relates to devices for detecting an analyte in a sample, comprising at least one matrix of electrodes according to the invention.

A subject of the present invention is also a method for detecting an analyte in a sample, comprising the following steps:

a) a conductive electroactive copolymer functionalized with oligonucleotides according to the invention or an electrode comprising a conductive support coated with a conductive electroactive copolymer functionalized with oligonucleotides according to the invention is provided, b) the electroactive copolymer or the electrode of step a) is brought into contact with the sample under reaction conditions that are suitable for the specific interaction of the analyte with said oligonucleotides, c) the analyte, attached to said oligonucleotides, is detected by means of an electrical measurement.

The invention therefore relates to the use of a copolymer, of an electrode or of a matrix of electrodes according to the invention, for detecting an analyte that may be present in a sample and that is capable of interacting specifically with the oligonucleotides according to the invention.

The term "analyte" is intended to mean any molecule capable of interacting specifically with oligonucleotides and therefore capable of being detected with a copolymer according to the invention. This analyte may be, for example, a biomolecule, for instance a protein, a peptide, a lipid, a steroid, a sugar or else a nucleic acid. The oligonucleotide carried by the copolymer is specific for the analyte to be detected. Advantageously, the oligonucleotide and the analyte to be detected form an antiligand/ligand (DNA/DNA, RNA/DNA, RNA/RNA or DNA/protein, for example) couple.

The present invention makes it possible to detect an analyte in any type of sample. In a particular embodiment of the invention, the sample is a biological sample. Advantageously, this sample may have been taken from a patient for diagnostic purposes. The sample may, for example, be urine, blood, serum, plasma, cell extracts or a body fluid.

In a preferred embodiment of the invention, a DNA and/or an RNA that hybridize(s) specifically to the oligonucleotides of the conductive electroactive copolymer according to the invention is (are) detected.

The copolymer of the present invention is an electroactive copolymer whose electrochemical response will be modified when an analyte interacts specifically with the oligonucleotides carried by the polymer. The conductive electroactive copolymer according to the invention therefore translates the interaction with the analyte into an electrochemical signal. The specific interaction of an analyte with the oligonucleotides carried by the copolymer engenders a modification of the electrochemical response of the copolymer studied, compared to a reference copolymer. Advantageously, the detection of the analyte is therefore carried out by means of an electrical measurement.

The term "electrical measurement" is intended to mean the measurement of a variation of potentiometric type such as the variation of the oxidation potential of the polymer, or the measurement of a variation of amperometric type by variation of the oxidation current observed at a given potential. These variations are measured rapidly, sensitively and quantitatively according to methods well known to those skilled in the art.

In an advantageous embodiment of the invention, the electrical measurement consists of the measurement of a variation of potential or of a variation of current. In a particular embodiment of the invention, cyclic voltammetry is used. This is an electroanalytical method that consists in sweeping a potential range in one direction and then in the other, at constant rate. The voltamperogram obtained gives the response, as current, of the electrochemical system studied and allows its characterization.

In a particularly advantageous embodiment of the invention, the detection of the specific interaction between the analyte and the oligonucleotides carried by the copolymer can be carried out with the electrode that was used for the electropolymerization of the polymer. For example, the hybridization of a nucleic acid complementary to the oligonucleotides of the copolymer can be detected by means of electrical measurement on the electrode that carries the copolymer according to the invention.

Methods of detection by means of an electrical measurement are preferred with the copolymers according to the invention. However, other conventional methods of detection known to those skilled in the art can also be used.

Another subject of the present invention consists of a substituted pyrrole of general formula (IV):

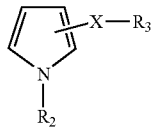

in which $R_2$ is an amine-protecting group. Various amine-protecting groups can be used in the substituted pyrroles according to the invention. These amine-protecting groups are well known to those skilled in the art (Kocienski P. J., Thieme Publishing Group, 1994). Preferably, the amine-protecting group is chosen from monomethoxytrityl, dimethoxytrityl, tosyl, triisopropylsilyl, tert-butoxycarbonyl, 9-fluorenyloxycarbonyl, benzyloxycarbonyl and acetyl.

$R_3$ is a phosphorus-comprising group capable of reacting with a free hydroxyl group. Preferably $R_3$ is chosen from a phosphotriester, H-phosphonate or phosphoramidite group, X represents a spacer arm chosen from —$(CH_2)_n$—O—, —$(CH_2)_p$—O—$[(CH_2)_2$—O$]_q$—, —$(CH_2)_r$—CO—NR'—$(CH_2)_{r'}$—O—, —$(CH_2)_r$—NCH$_3$—$(CH_2)_{r'}$—O—, —$(CH_2)_r$—CO—NR'—$[(CH_2)_2$—O$]_s$—, —$(CH_2)_r$—NCH$_3$—$[(CH_2)_2$—O$]_s$—, R' represents —H or —CH$_3$, n is an integer between 1 and 5,
p is an integer between 1 and 2,
q is an integer between 1 and 4,
r is an integer between 1 and 3,
r' is an integer between 1 and 3,
s is an integer between 1 and 3,
n, p, q, r, r' and s are identical or different,
the pyrrole ring is substituted in the 2-, 3-, 4- or 5-position.

In a preferred embodiment, the invention relates to a substituted pyrrole of general formula (V):

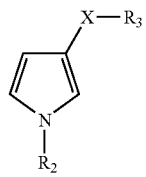

in which $R_2$ is an amine-protecting group. Preferably, $R_2$ is chosen from monomethoxytrityl, dimethoxytrityl, tosyl, triisopropylsilyl, tert-butoxycarbonyl, 9-fluorenyloxycarbonyl, benzyloxycarbonyl and acetyl.

$R_3$ is a phosphorus-comprising group capable of reacting with a free hydroxyl group. Preferably, $R_3$ is chosen from a phosphotriester, H-phosphonate or phosphoramidite group, X represents a spacer arm chosen from —$(CH_2)_n$—O—, —$(CH_2)_p$—O—$[(CH_2)_2$—O$]_q$—, —$(CH_2)_r$—CO—NR'—$(CH_2)_{r'}$—O—, —$(CH_2)_r$—NCH$_3$—$(CH_2)_{r'}$—O—, —$(CH_2)_r$—CO—NR'—$[(CH_2)_2$—O$]_s$—, —$(CH_2)_r$—NCH$_3$—$[(CH_2)_2$—O$]_s$—, R' represents —H or —CH$_3$,
n is an integer between 1 and 5,
p is an integer between 1 and 2,
q is an integer between 1 and 4,
r is an integer between 1 and 3,
r' is an integer between 1 and 3,
s is an integer between 1 and 3,
n, p, q, r, r' and s are identical or different.

Preferably, $R_2$ represents monomethoxytrityl. Preferably, $R_3$ represents a phosphoramidite group. In a preferred embodiment of the invention, X represents —$(CH_2)_n$—O— and n is equal to 2.

In another embodiment of the invention, the substituted pyrrole corresponds to general formula (VI):

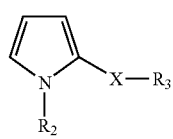

in which $R_2$ is an amine-protecting group, preferably chosen from monomethoxytrityl, dimethoxytrityl, tosyl, triisopropylsilyl, tert-butoxycarbonyl, 9-fluorenyloxy-carbonyl, benzyloxycarbonyl and acetyl, $R_3$ is a phosphorus-comprising group capable of reacting with a free hydroxyl group. Preferably, $R_3$ is chosen from a phosphotriester, H-phosphonate or phosphoramidite group, X represents a spacer arm chosen from $-(CH_2)_n-$, $-(CH_2)_p-O-[(CH_2)_2-O]$, $-(CH_2)_r-CO-NR'-(CH_2)_{r'}-O-$, $-(CH_2)_r-NCH_3-(CH_2)_{r'}-O-$, $-(CH_2)_r-CO-NR'-[(CH_2)_2-O]_s-$, $-(CH_2)_r-NCH_3-[(CH_2)_2-O]_s-$, R' represents —H or —CH$_3$, n is an integer between 1 and 5, p is an integer between 1 and 2, q is an integer between 1 and 4, r is an integer between 1 and 3, r' is an integer between 1 and 3, s is an integer between 1 and 3, n, p, q, r, r' and s are identical or different.

Preferably, $R_2$ represents monomethoxytrityl. Preferably, $R_3$ represents a phosphoramidite group. In a preferred embodiment of the invention, X represents $-(CH_2)_n-O-$ and n is equal to 2.

Another subject of the present invention consists of a method for preparing a pyrrole substituted with an oligonucleotide of general formula (I)

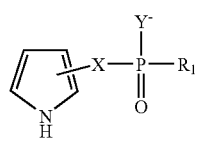

in which $R_1$, X and Y are as defined above, comprising the following steps:

a) the cycles for synthesizing an oligonucleotide are carried out, b) in the final cycle for synthesizing said oligonucleotide, a substituted pyrrole of general formula (IV)

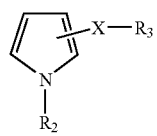

in which $R_2$, $R_3$ and X are as defined above, is substituted at the final nucleotide in the 5' position or in the 3' position of said oligonucleotide;

c) said protective group $R_2$ is cleaved.

In an advantageous embodiment of the invention, the protective group $R_2$ is monomethoxytrityl and, in step c), this protective group is cleaved by means of a treatment in an acid medium.

In a preferred embodiment, the protective group $R_2$ is monomethoxytrityl and the oligonucleotide is purified by reverse phase chromatography, before cleaving the protective group in step c).

The substitution of a substituted pyrrole of general formula (IV) is carried out following the cycles of synthesizing the oligonucleotide. In the final cycle of synthesis, the nucleotide is replaced with a substituted pyrrole of general formula (IV).

According to a first example, in the "H-phosphonate" serial cycle as represented in the scheme below, the final nucleotide of this cycle is replaced with a substituted pyrrole of formula (IV) according to the invention, in which the phosphorus-comprising group is an H-phosphonate.

"H-phosphonate" serial cycle

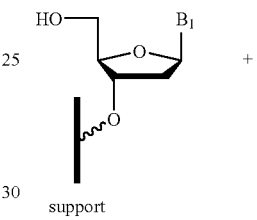

support

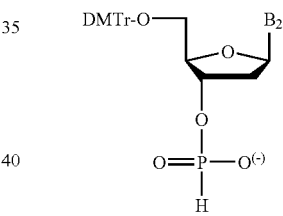 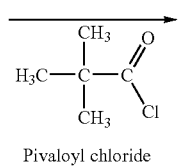

Pivaloyl chloride

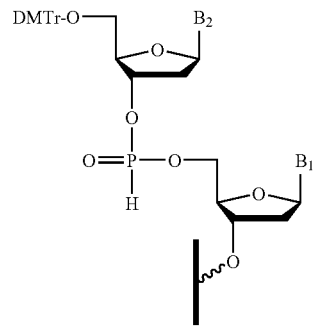

According to another example, in the case of the phosphoramidite condensation cycle as represented in the scheme below, the final nucleotide of this chain is replaced with the substituted pyrrole of formula (IV) according to the invention, in which the phosphorus-comprising group is a phosphoramidite.

Y=O or S
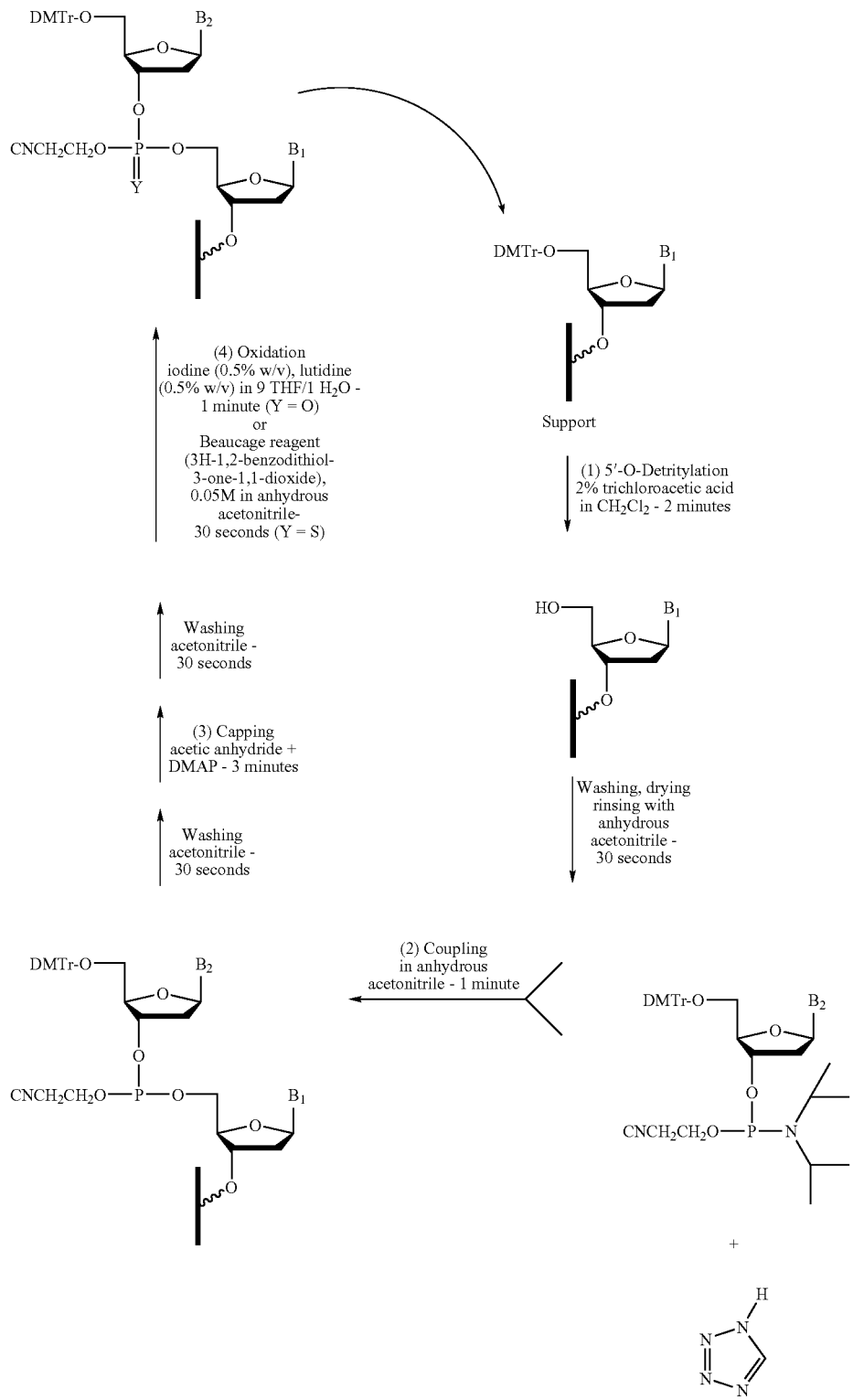
Similarly, according to another example, in the case of the "phosphotriester" condensation cycle as represented in the scheme below, the final nucleotide of this cycle is replaced with a substituted pyrrole of formula (IV) according to the invention, in which the phosphorus-comprising group is a phosphodiester.

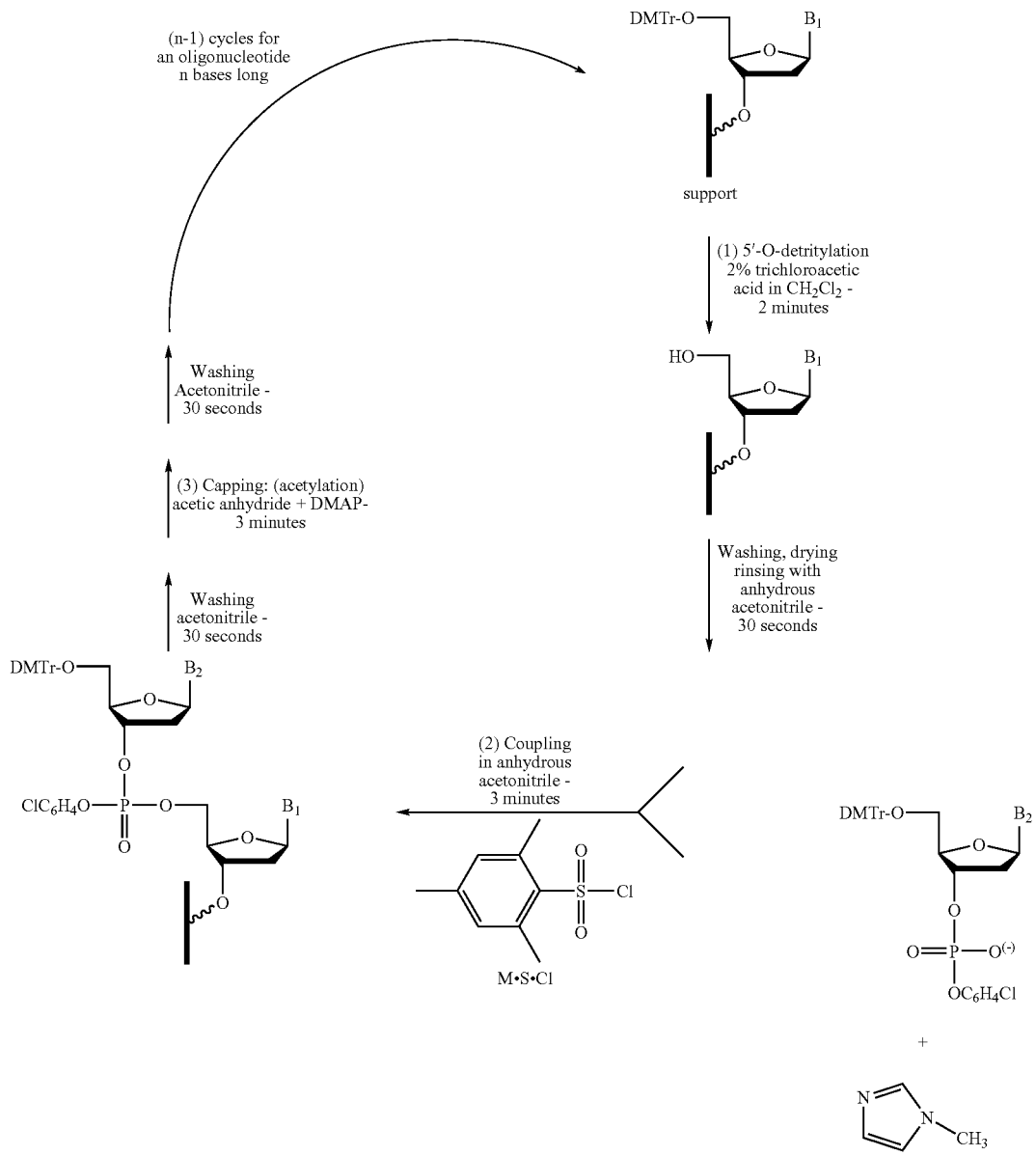

Phosphotriester condensation cycle

At the end of the cycles of synthesizing the 5 oligonucleotide, and after deprotection, the free hydroxyl at the 5' or 3' end of the oligonucleotide reacts with the reactive phosphorus (phosphodiester, phosphoramidite, H-phosphonate) of the substituted pyrrole of general formula (IV).

DESCRIPTION OF THE FIGURES

FIG. 1A Sequence of the oligonucleotide:

5'ttt ttt ttt ttg cct tga cga tac agc ta (SEQ ID NO: 1), retention time (Rt): 14.87 min.

FIG. 1B Sequence of the oligonucleotide:

5'pyrrole tosyl—ttt ttt ttt ttg cct tga cga tac agc ta (SEQ ID NO: 1), Rt: 16.35 min.

FIG. 1C Coinjection of the 2 oligonucleotides (Rt: 15.07 min and 17.40 min).

Figure 2:
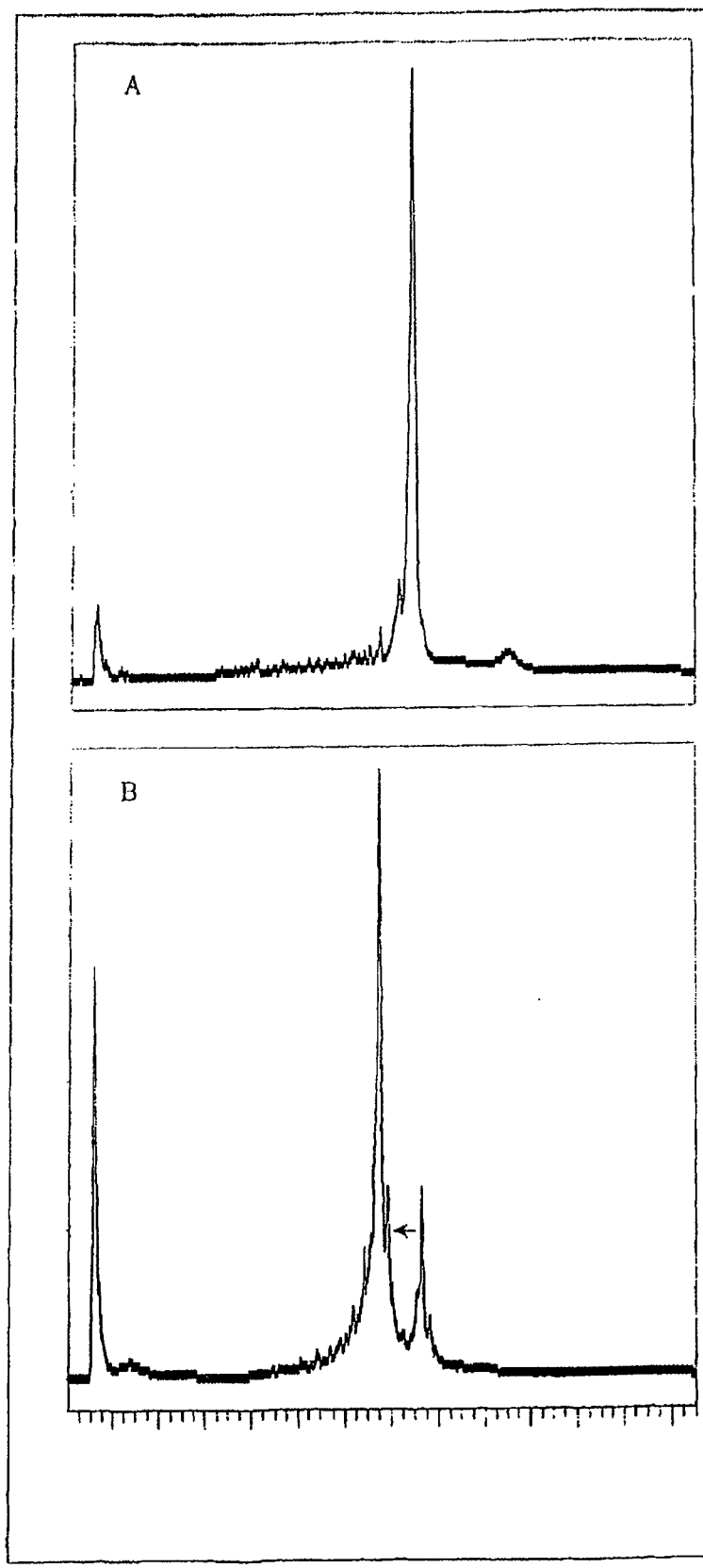

FIG. 2: HPLC monitoring of the cleavage of the tosyl group.

FIG. 2A Sequence of the oligonucleotide:

5'pyrrole tosyl—ttt ttt ttt ttg cct tga cga tac agc ta (SEQ ID NO: 1), Rt: 14.9 min.

FIG. 2B Sequence of the oligonucleotides:

5'pyrrole tosyl—ttt ttt ttt ttg cct tga cga tac agc ta (SEQ ID NO: 1) (20%), Rt: 15.25 min, 5'pyrrole—ttt ttt ttt ttg cct tga cga tac agc ta (SEQ ID NO: 1) (80%), Rt: 13.48 min. after 24 h in a 0.5 M NaOH solution at 55° C.

Figure 3:
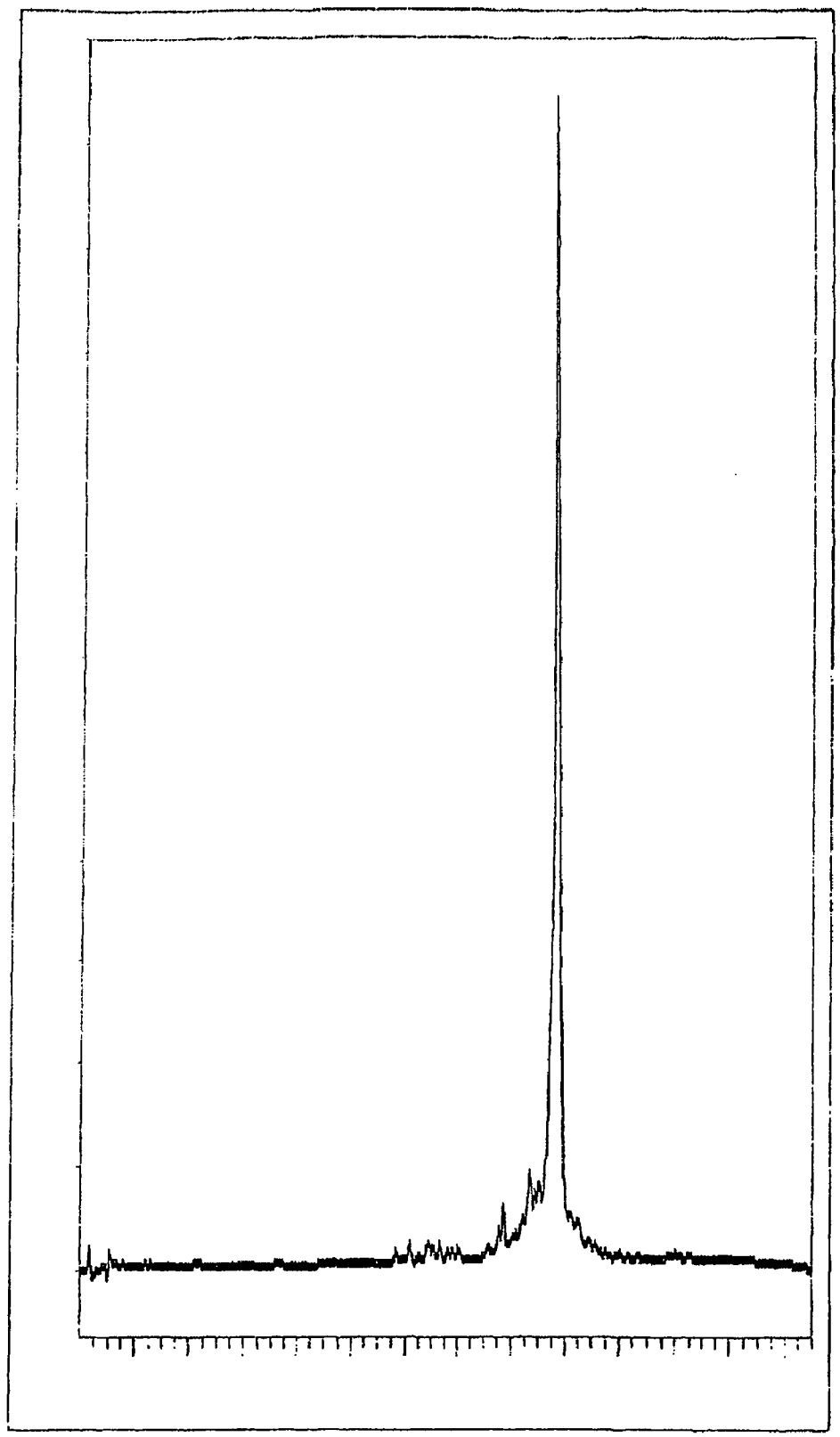

FIG. 3: Chromatogram of the purified oligonucleotide carrying the pyrrole substituted in the 3-position and synthesized from the pyrrole monomer carrying the MMT. Sequence of the oligonucleotide: 5'pyrrole—at ctc ggg aat ctc aat gtt ag (SEQ ID NO: 2), RT: 17.6 min.

Figure 4:
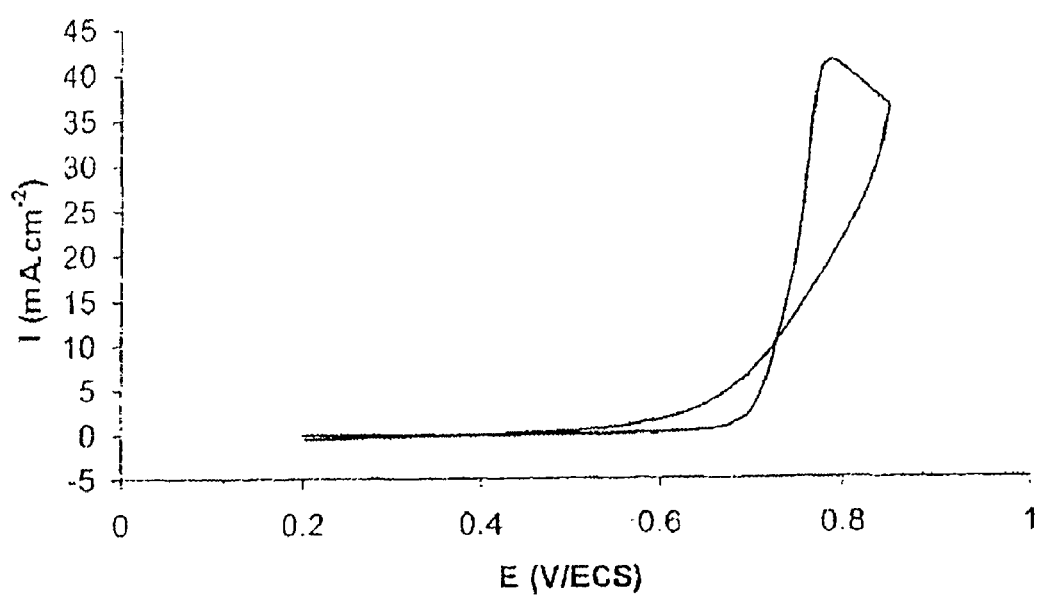

FIG. 4: First cycle of cyclic voltammetry for a solution of 3-(hydroxyethyl)pyrrole on a platinum electrode.

Figure 5:
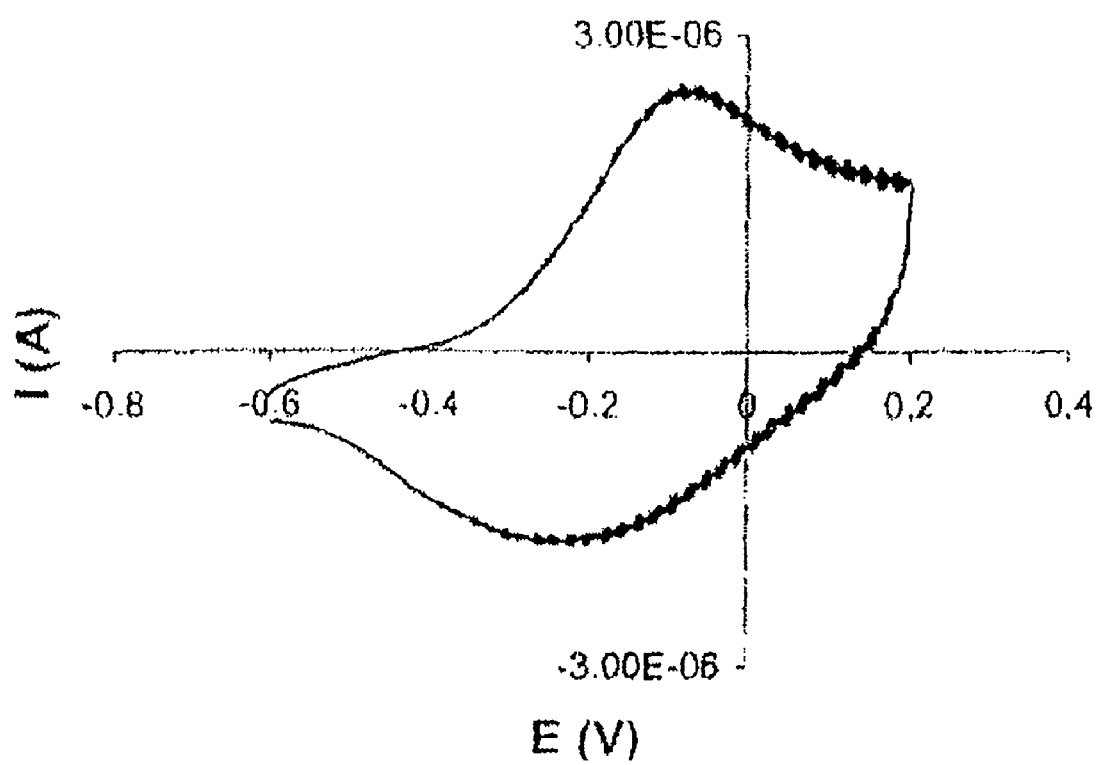

FIG. 5: Cyclic voltammetry curve for an electrode modified with a polymeric film of 3-(hydroxyethyl)-pyrrole transferred into the electrolyte free of monomers.

Figure 6:
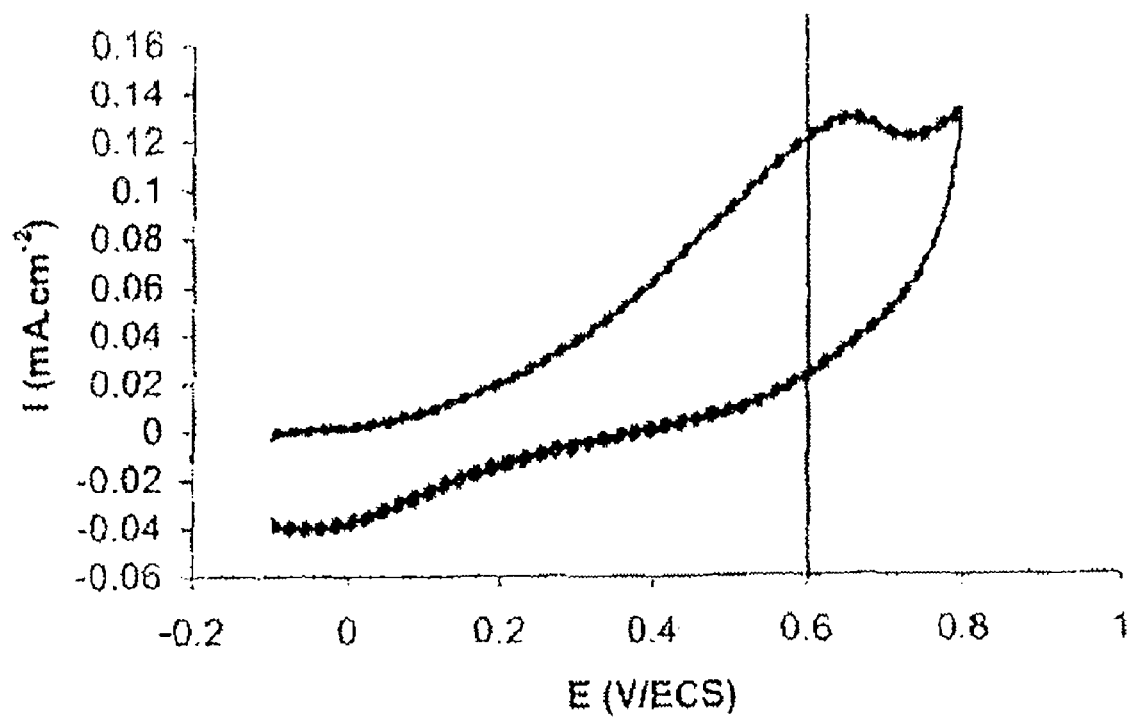

FIG. 6: First cycle of cyclic voltammetry in a 5 µM solution of pyrrole-ODN in the 3-position, on a platinum electrode.

Figure 7:
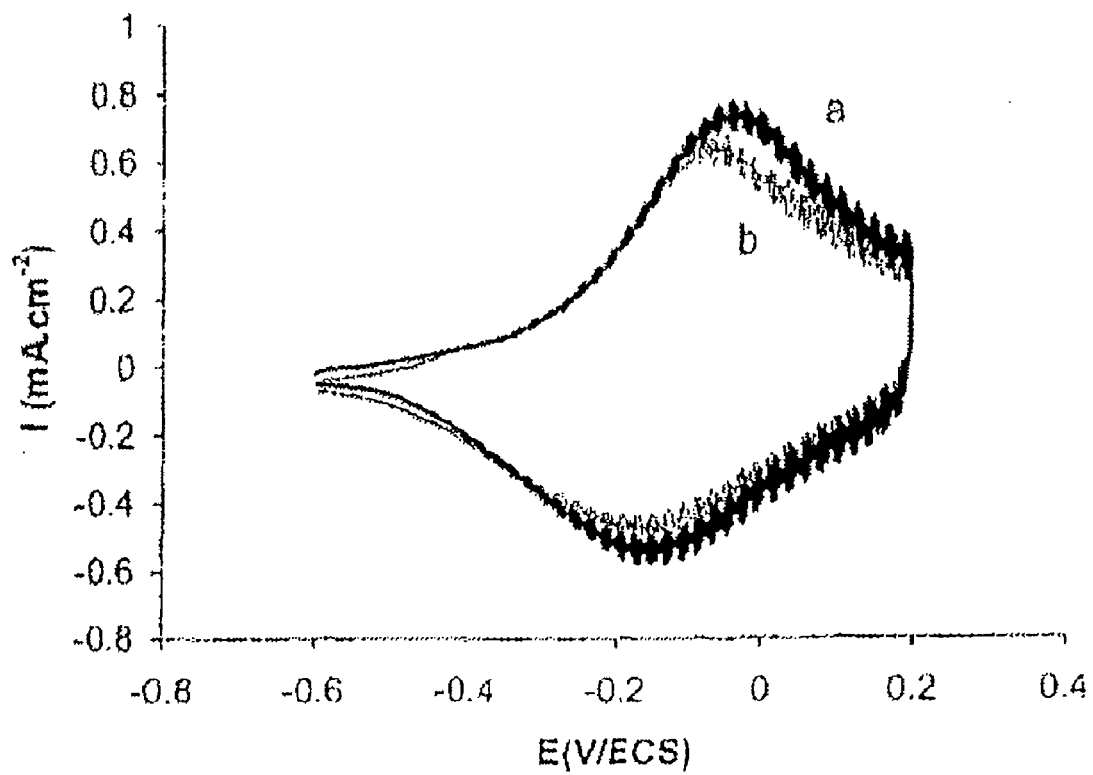

FIG. 7: Cyclic voltammetry curve for an electrode modified with a film of pyrrole-ODN in the 3-position, on a prefilm of 3-(hydroxyethyl)pyrrole, transferred into the electrolyte solution free of monomers.

Figure 8:
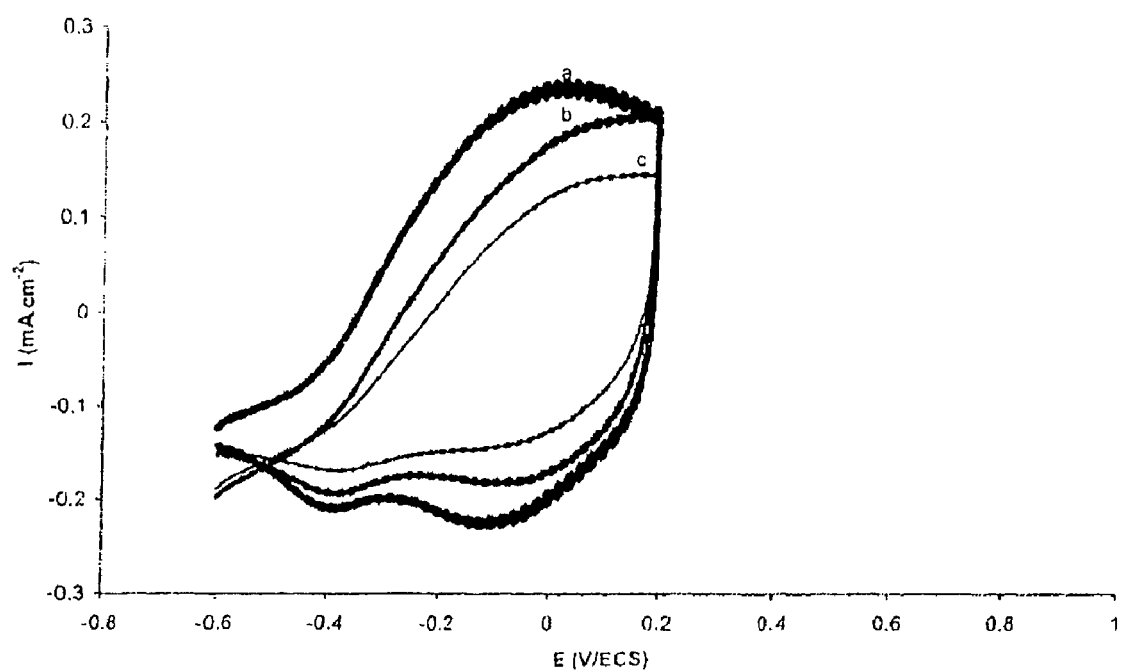

FIG. 8: Modification of the electrochemical signal of the modified electrode subjected to various media.

Figure 9:
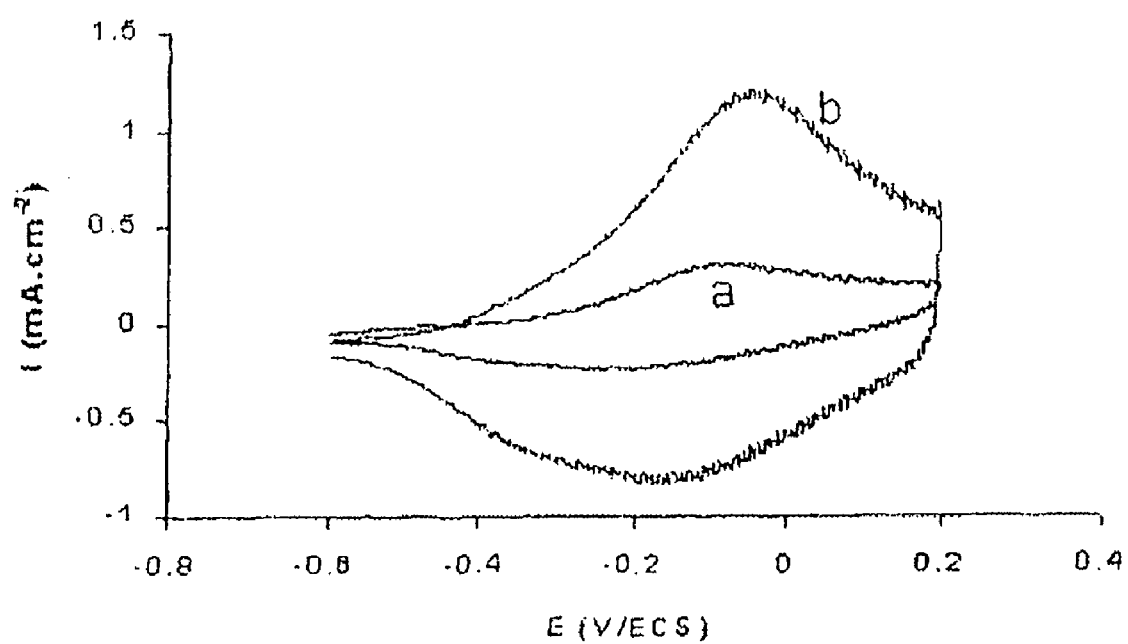

FIG. 9: Cyclic voltammetry curve for an electrode modified with a copolymer on a prefilm transferred into the electrolyte solution free of monomers.

Figure 10:
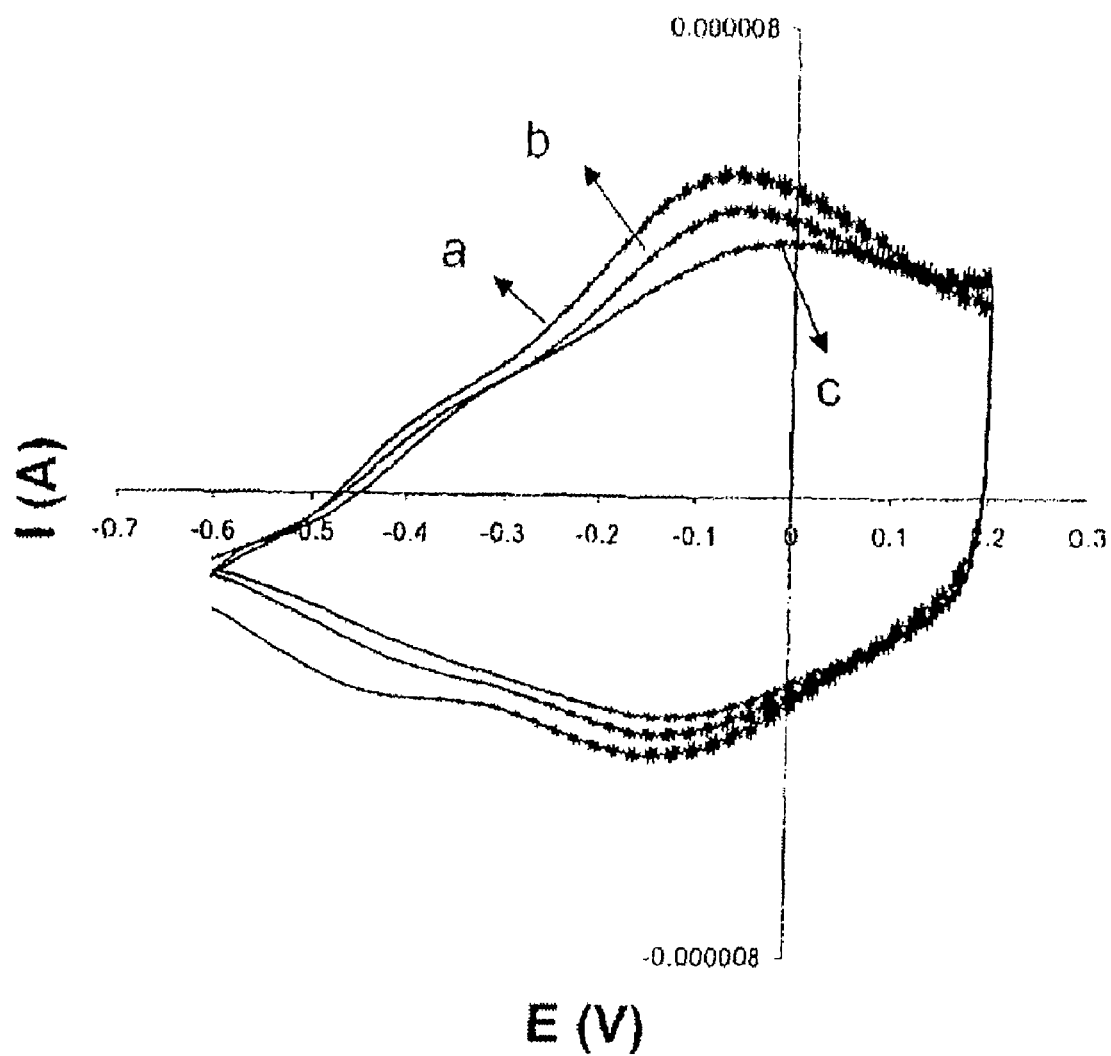

FIG. 10: Modification of the electrochemical signal of the modified electrode subjected to various media.

FIG. 11: Modification of the electrochemical signal of the electrode modified with a copolymer subjected to various media.

EXAMPLES

Example 1

Synthesis of 1-(N-tosyl)-3-(hydroxyethyl)-pyrrole 1-(N-Tosyl)-3-(hydroxyethyl)pyrrole can be obtained according to the following synthesis:

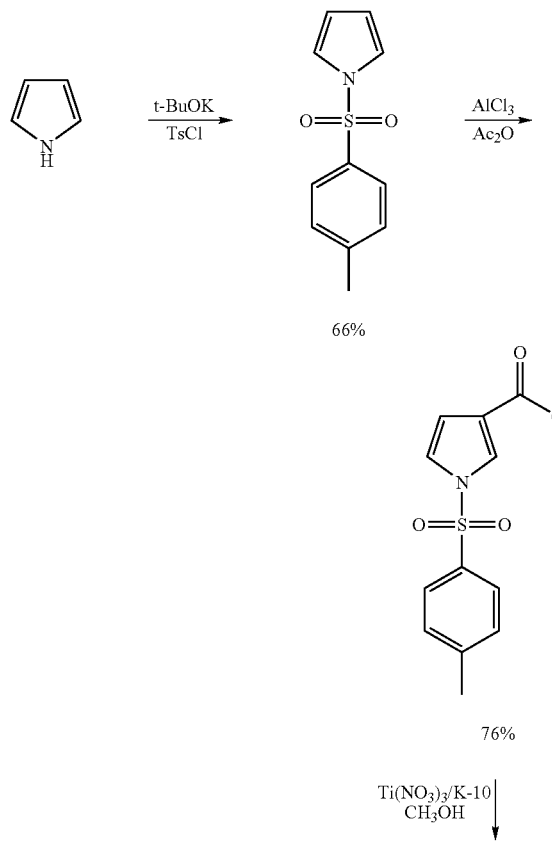

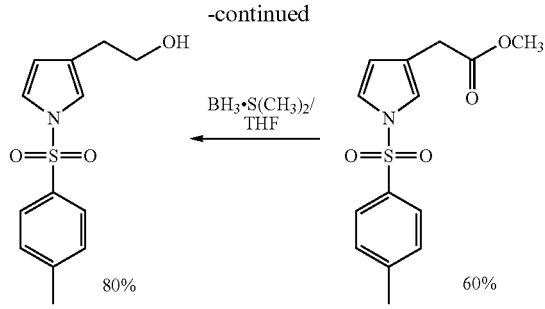

The synthesis of 1-(N-tosyl)-3-(hydroxyethyl)pyrrole was carried out as described by Korri-Youssoufi et al., Materials Science and Engineering C15 (2001) 265-268. In a first step, 1-(N-tosyl) pyrrole was synthesized from pyrrole using tosyl chloride in the presence of a strong base, potassium tert-butoxide. Next, acylation of the 1-(N-tosyl)pyrrole with acetic anhydride made it possible to obtain 1-tosyl-3-acetylpyrrole, which was converted to methyl 2-[3-(1-N-tosylpyrrole)] acetate by oxidative transposition, using thallium nitrate in the presence of montmorillonite. Reduction under mild conditions with borane dimethyl sulfide gave the desired product, 1-(N-tosyl)-3-(hydroxyethyl)pyrrole. The overall yield of the reaction was 21.8%.

Example 2

Synthesis of 1-[N-(p-monomethoxytrityl)]-3-(hydroxyethyl)pyrrole

1-[N-(p-Monomethoxytrityl)]-3-(hydroxyethyl)pyrrole was obtained according to the following synthesis:

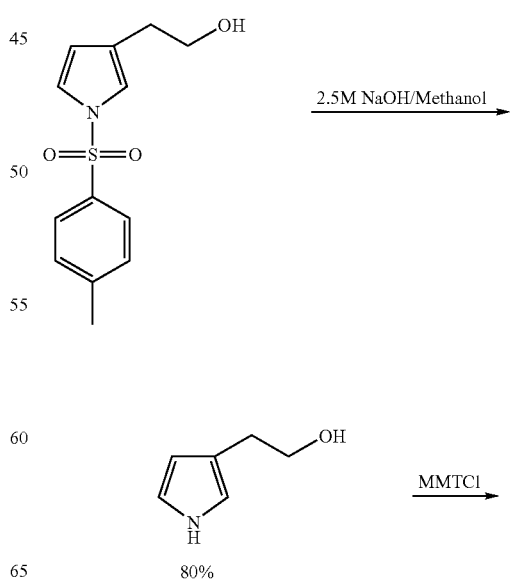

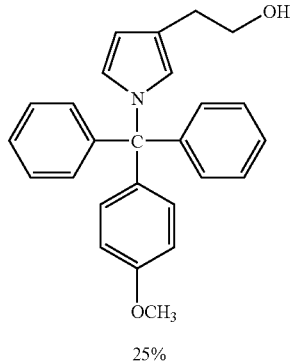

25%

The nitrogen of 1-[N-tosyl]-3-(hydroxyethyl)pyrrole is deprotected in a conventional manner with a solution of sodium hydroxide (2.5 M NaOH/methanol), for two hours at reflux. After extraction of the 3-(hydroxyethyl)-pyrrole with ethyl ether and concentration of the product to dryness, monomethoxytritylation of the amine function is then carried out with monomethoxytrityl chloride (1.2 equivalents), in dichloromethane anhydride, in the presence of 1 equivalent of TEA. After purification on a silica column, the expected product, 1-[N-(p-monomethoxytrityl)]-3-(hydroxyethyl)-pyrrole, was obtained with a 25% yield.

$^1$H NMR of 1-[N-(p-monomethoxytrityl)]-3-(hydroxyethyl)-pyrrole: δ ppm (CDCl$_3$)=7.28-6.75 (m, 16H, Ar MMtr, H-2, H-5); 5.88 (t, 1H, H-4); 3.79 (s, 3H, OCH$_3$); 3.73 (t, 2H, 2×H-7); 2.7 (t, 2H, 2×H-6).

Example 3

Synthesis of 1-[N-(tosyl)]-3-[7-O-(2-cyano-ethyl-N, N-diisopropylphosphoramidityl)hydroxyethyl]-pyrrole The 1-[N-(tosyl)]-3-[7-O-(2-cyanoethyl-N,N-diisopropyl-phosphoramidityl)hydroxyethyl]pyrrole was obtained according to the following synthesis:

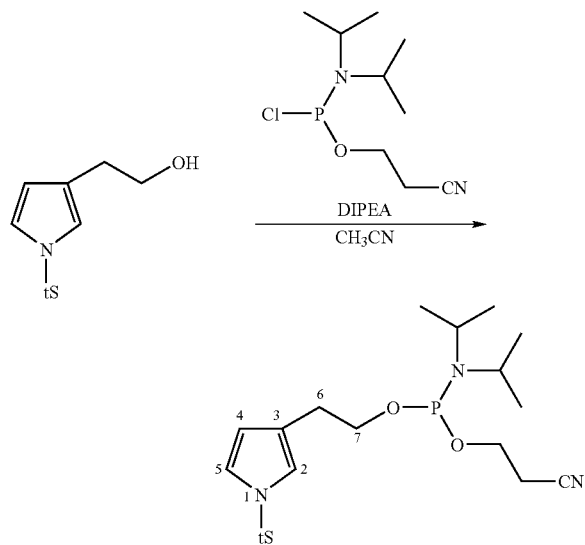

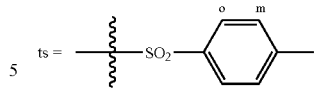

1-(N-Tosyl)-3-(hydroxyethyl)pyrrole (50 mg, 187.5 μmol, 1 eq.) was coevaporated 3 times with anhydrous aceto-nitrile, and was then dissolved in 1 ml of aceto-nitrile. The round-bottomed flask was placed under an inert atmosphere and 68 μl (48 mg, 375 μmol, 2 eq.) of DIPEA (diisopropylethylamine) were added. Chloro-phosphine (48 μl, 72 mg, 275 μmol, 1.1 eq.) was added dropwise and the entire mixture was left for 5 minutes with stirring. The reaction mixture was then concentrated to one half its volume in a rotary evaporator and was loaded onto a column of silica gel poured in a cyclohexane/triethylamine (99:1) mixture and rinsed with cyclohexane. The product was subsequently eluted with a cyclohexane/ethyl acetate (80:20) mixture. The correct fractions were then combined and concentrated. The yellow oil obtained was taken up in acetonitrile, filtered through a millex PVDF 0.22 μm filter and reconcentrated to obtain 67 mg (144 μmol, 77%) of product.

TLC: Rf=0.5 cyclohexane/ethyl acetate (50:50) $^{31}$P NMR: 148.32 ppm $^1$H NMR: δ ppm (CD$_3$CN)=7.75 (d, 2H, J=8 Hz, H-o); 7.35 (d, 2H, J=8 Hz, H-m); 7.05 (m, 2H, H-2+H-5); 6.20 (s, 1H, H-4); 3.69 (m, 6H, O—CH$_2$—CH$_2$—CN+2× NCH(CH$_3$)$_2$+2×H-7); 2.60 (m, 4H, 2×H-6+O—CH$_2$—CH$_2$—CN); 2.37 (s, 3H, CH$_3$-Ph); 1.10 (m, 12H, 2×NCH (CH$_3$)$_2$).

Example 4

Synthesis of 1-[N-(p-monomethoxytrityl)]-3-[7-O-(2-cyanoethyl-N,N-diisopropylphosphoramidityl)-hydroxyethyl]pyrrole The synthesis of 1-[N-(p-monomethoxytrityl)]-3-[7-O-(2-cyanoethyl-N,N-diisopropylphosphoramidityl)hydroxyethyl]pyrrole was carried out according to the following scheme:

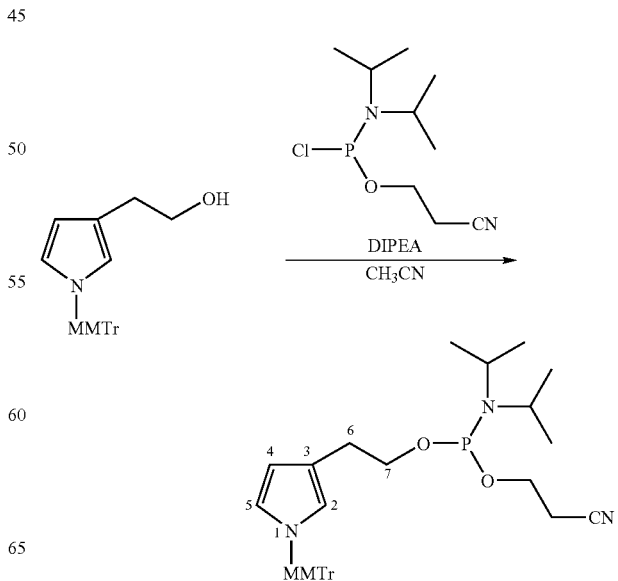

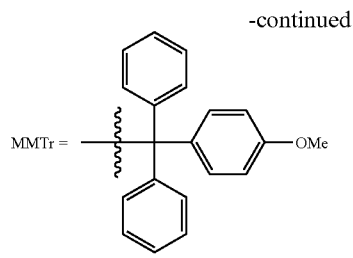

1-[N-[p-Monomethoxytrityl)]-3-(hydroxyethyl)pyrrole (120 mg, 300 μmol, 1 eq.) was coevaporated 3 times with anhydrous acetonitrile, and then dissolved in 2 ml of acetonitrile. The round-bottomed flask was placed under an inert atmosphere and 160 μl (114 mg, 600 μmol, 2 eq.) of DIPEA (diisopropylethylamine) were added. Chlorophosphine (82 μl, 87 mg, 330 μmol, 1.1 eq.) was added dropwise and the entire mixture was left for 5 minutes with stirring. The reaction mixture was then concentrated to half its volume in a rotary evaporator and was loaded onto a column of silica gel poured in a cyclohexane/triethylamine (99:1) mixture and rinsed with cyclohexane. The product was subsequently eluted with a cyclohexane/ethyl acetate (90:10) mixture. The correct fractions were then combined and concentrated. The yellow oil obtained was taken up in acetonitrile, filtered through a millex PVDF 0.22 μm filter and reconcentrated to obtain 120 mg (205 μmol, 68%) of product.

TLC: Rf=0.3 cyclohexane/ethyl acetate (50:50) $^{31}$P NMR: 147.15 ppm $^1$H NMR: δ ppm (CD$_3$CN)=7.09 (m, 15H, MMTr+H-5); 6.80 (d, 1H, J=8.9 Hz, H-2); 6.51 (s, 1H, H-4); 3.63 (m, 9H, OCH$_3$+O—CH$_2$—CH$_2$—CN+2×NCH(CH$_3$)$_2$+ 2×H-7); 2.67 (m, 4H, 2×H-6+O—CH$_2$—CH$_2$—CN); 1.10 (m, 12H, 2×NCH(CH$_3$)$_2$).

Example 5

Synthesis of 1-(N-tosyl)-3-[2-(triethyloxy)-hydroxyethyl)]pyrrole 1-(N-Tosyl)-3-[2-(triethyloxy)hydroxyethyl)]pyrrole was synthesized according to the following reaction scheme:

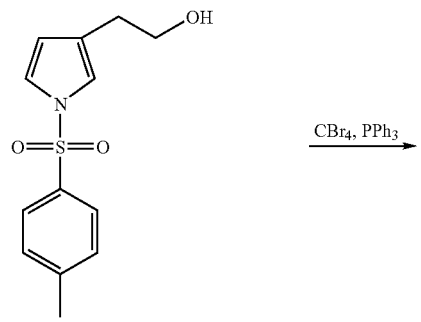

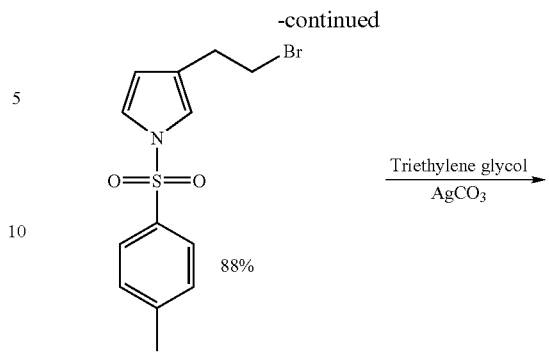

The alcohol function of 1-(N-tosyl)-3-(hydroxyethyl)-pyrrole was substituted with a bromine in the presence of CBr$_4$ and of triphenylphosphine, at 0° C. in anhydrous acetonitrile. The triethylene glycol arm was then coupled by nucleophilic substitution in a basic medium. The overall yield of the reaction was 24.6%.

$^1$H NMR of 1-(N-tosyl)-3-[2-(triethyloxy)hydroxyethyl)]-pyrrole: δ ppm (CDCl$_3$)=7.65 (d, 2H, 2×H Ts); 7.20 (d, 2H, 2×H Ts); 6.98 (t, 1H, H-5); 6.9 (s, 1H, H-2); 6.11 (d, 1H, H-4); 3.65-3.5 (m, 14H, 7×CH$_2$—O); 2.60 (t, 2H, 2×H-6); 2.33 (s, 3H, CH$_3$ Ts)

Example 6

Synthesis of 1-(N-tosyl)-2-(hydroxyethyl)-pyrrole 1-(N-Tosyl)-2-(hydroxyethyl)pyrrole was synthesized according to the following reaction scheme:

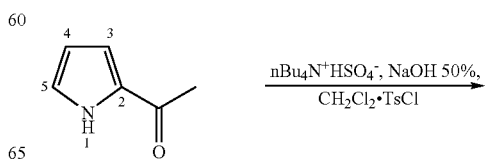

-continued

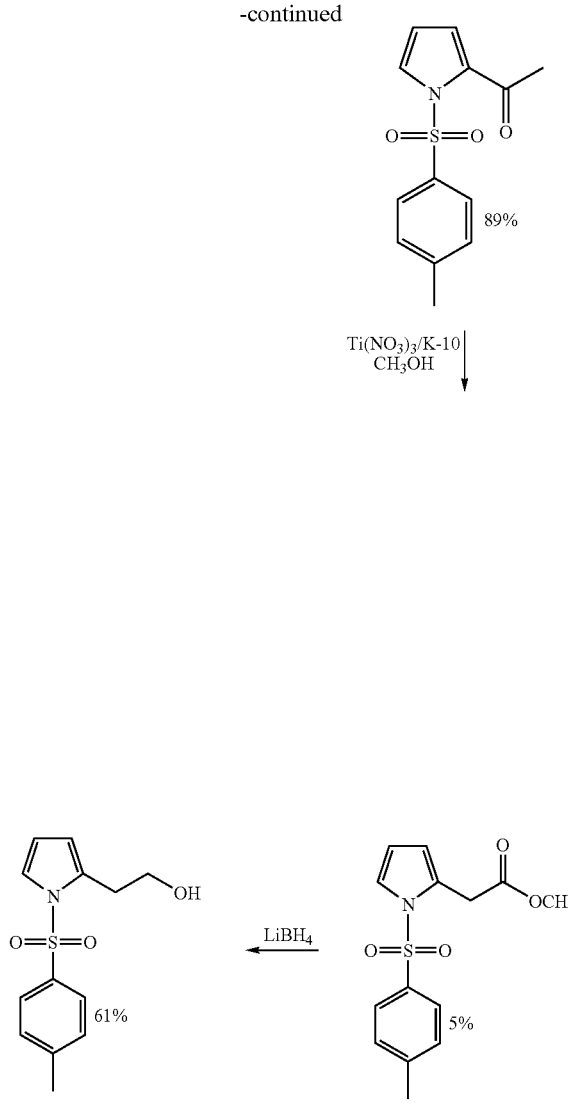

The tosyl group was introduced in the 1-position of the 2-acetylpyrrole by reaction with tosyl chloride, at 0° C. in dichloromethane, in the presence of n-butylammonium sulfate and of sodium hydroxide. Methyl 2-[2-(1-N-tosylpyrrole)]acetate was then obtained by oxidative transposition using thallium nitrate in the presence of montmorillonite. A step consisting of reduction with LiBH$_4$ gives the desired product, 1-(N-tosyl)-2-(hydroxyethyl)pyrrole. The overall yield of the synthesis was 3%.

$^1$H NMR of 1-(N-tosyl)-2-(hydroxyethyl)pyrrole: δ ppm (CDCl$_3$)=7.64 (d, 2H, 2×H Ts); 7.31 (d, 2H, 2×H Ts); 7.27 (d, 1H, H-5); 6.22 (t, 1H, H-4); 6.10 (s, 1H, H-3); 3.80 (t, 2H, 2×H-6); 2.95 (t, 2H, 2×H-7); 2.40 (s, 3H, CH$_3$ Ts).

Example 7

Synthesis of an Oligonucleotide on a Solid Support

An oligonucleotide was synthesized on a solid support (controlled pore glass, CPG) by the phosphoramidite method described by Beaucage and Lyer, (Tetrahedron, 48, 223-2311, 1992).

The first nucleoside of the sequence to be synthesized is attached to the solid support (CPG) in the 3'-position, the 5'OH end of the nucleoside being protected with a dimethoxytrityl (DMT) acid-labile group.

In a first step consisting of detritylation, acid treatment (tri- or dichloroacetic acid) makes it possible to remove the DMT group in order to generate the reactive 5'OH end.

In a second step consisting of "coupling", the phosphoramidite of the base to be added is condensed with this first nucleoside in order to generate a phosphite triester bond. The condensation is carried out in the presence of a catalyst (tetrazole or S-thioethyltetrazole, or DCI, or etc.).

In a third step consisting of "capping", the 5'OH ends that have not reacted during the preceding condensation step are blocked with an acylating reagent (acetic anhydride) in order to prevent deletions in the sequence.

In a fourth step consisting of oxidation, the phosphite triester bond is oxidized to a phosphate triester bond by means of an oxidative treatment (aqueous iodine). The phosphite triester bond can also be oxidized using the Beaucage reagent in solution in acetonitrile, to give a phosphorothioate triester bond.

Steps 1 to 4 are repeated as often as necessary according to the length of the sequence to be synthesized. These 4 steps constitute one cycle of synthesis.

When the desired sequence is complete, the solid support to which the oligonucleotide is attached is incubated in a concentrated aqueous ammonia solution in order to cleave the oligonucleotide from the support, and to deprotect the bases and the phosphate groups.

Example 8

Figure 1:
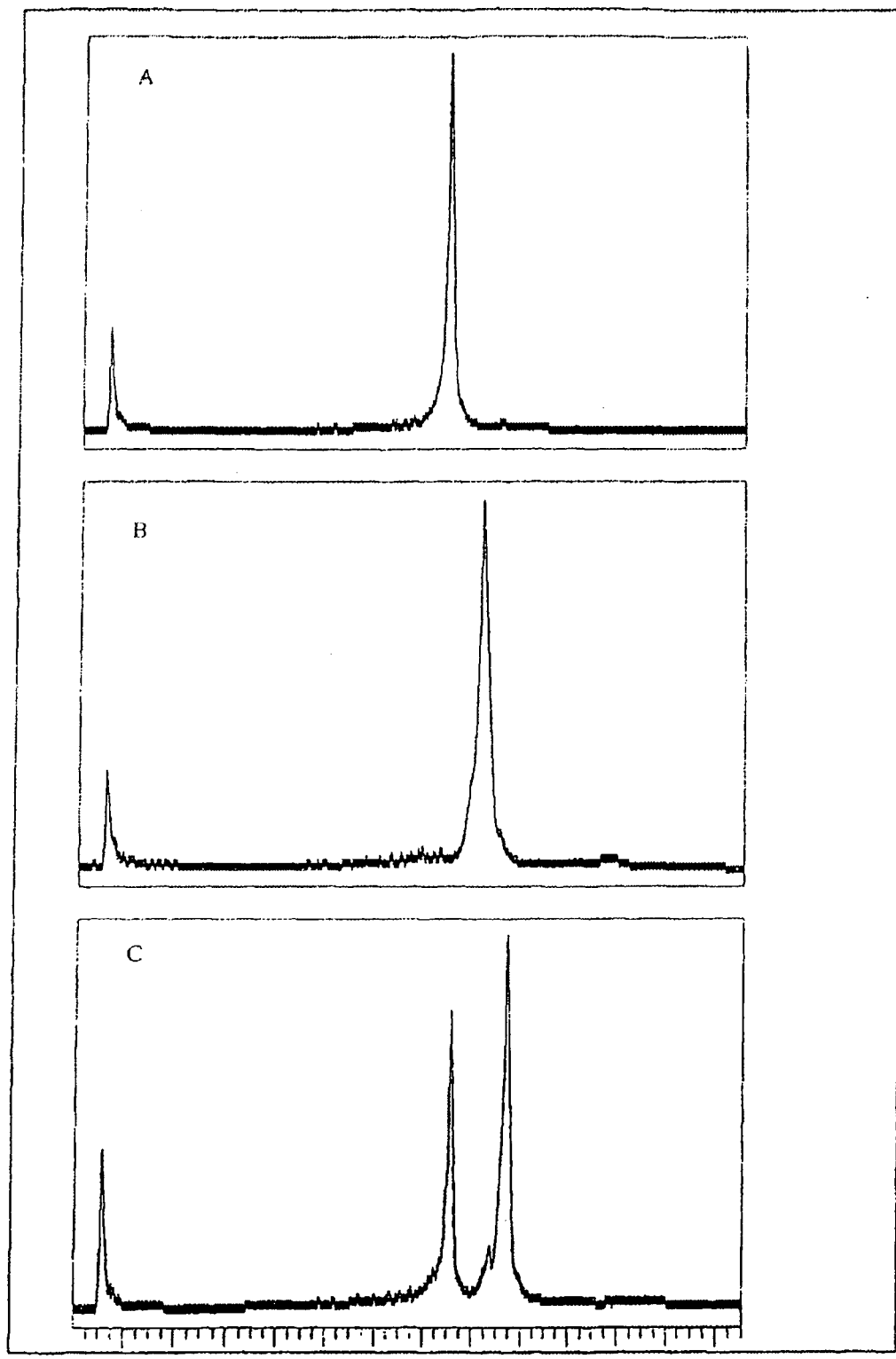
FIG. 1: Chromatograms of the 5'OH oligonucleotide before and after incorporation of 1-[N-(tosyl)]-3-[7-O-(2-cyanoethyl-N,N-diisopropylphosphoramidityl)hydroxyethyl].

Incorporation of Pyrrole Substituted in the 3-position, Protected on the Nitrogen with a Tosyl Group, at the 5' End of an Oligonucleotide A final cycle of synthesis was carried out using the pyrrole monomer 1-[N-(tosyl)]-3-[7-O-(2-cyanoethyl-N,N-diisopropylphosphoramidityl) hydroxyethyl]pyrrole, the synthesis of which is described in Example 3 above. This monomer was used under exactly the same conditions as a conventional nucleotide synthon, the only difference being the coupling time, which is 15 minutes instead of 1.3 minutes in order to take into account any possible problems of incorporation. The reaction scheme is represented below. After deprotection in 30% aqueous ammonia (16 h at 55° C.), the crude oligonucleotide was analyzed by ion exchange HPLC (FIG. 1). FIG. 1 represents the coinjection of the oligo with and without pyrrole so as to demonstrate the incorporation. (Gradient of 400 to 640 mM NaCl in 20 min, Gen Pack Fax™ column (Waters™), 0.75 ml/min).

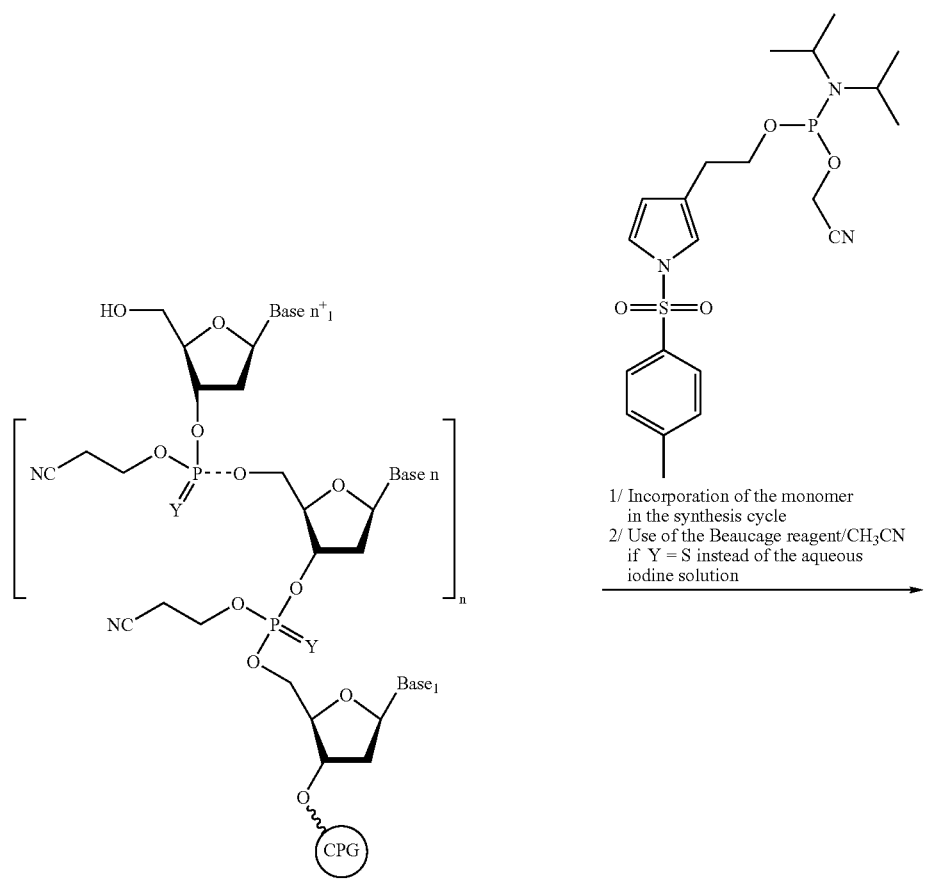
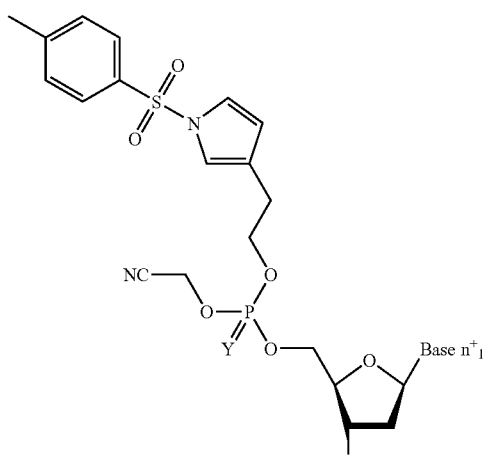

-continued
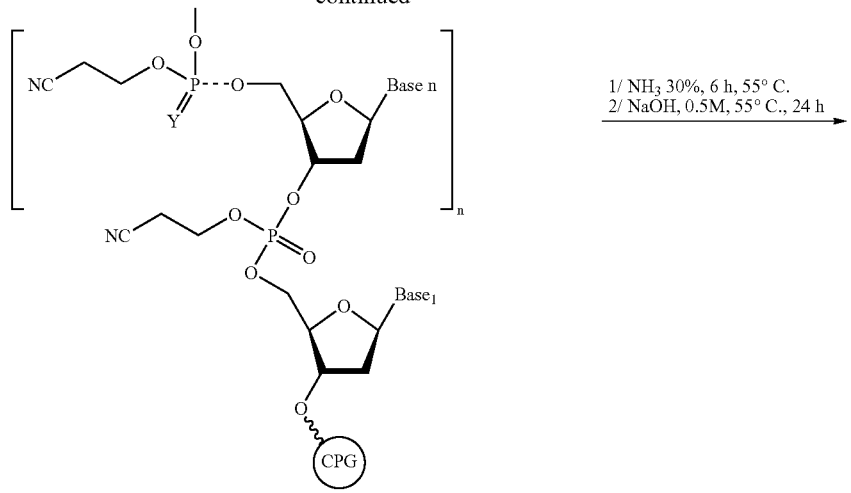
1/ NH₃ 30%, 6 h, 55° C.
2/ NaOH, 0.5M, 55° C., 24 h
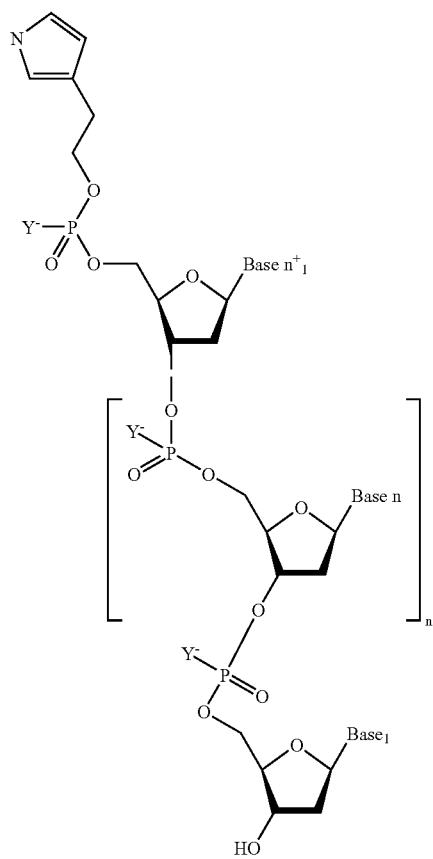
Y = O or S

Example 9

Cleavage of the Tosyl Group and Purification of the Oligonucleotide

The tosyl group is eliminated in 4 hours in a 2.5 M sodium hydroxide solution at 75° C., but under these conditions, the oligonucleotide is completely degraded. We therefore used milder hydrolysis conditions (0.5 M NaOH solution at 55° C. for 24 h) in order to prevent degradation of the oligonucleotide while at the same time obtaining 80% cleavage of the tosyl group carried by the pyrrole. It was then possible, by HPLC, to separate the 2 oligonucleotides so as to isolate the completely deprotected oligonucleotide (FIG. 2). FIG. 2 represents the cleavage of the tosyl in 0.5 M NaOH medium, 55° C. (gradient of 440 to 680 mM NaCl in 20 min. Gen Pack Fax™ column (Waters™), 0.75 ml/min).

When the oligonucleotide is not purified by HPLC, the sodium hydroxide can be eliminated by simple precipitation with acetone, and said oligonucleotide can be used as it is for the copolymerization experiments.

Example 10

Incorporation of Pyrrole Substituted in the 3-position, Protected on the Nitrogen with a Monomethoxytrityl Group, at the 5' End of an Oligonucleotide A final cycle of synthesis was carried out using the pyrrole monomer, the synthesis of which is described in Example 4 above. This monomer is used under exactly the same conditions as a conventional base, the only difference being the coupling time, which is 15 minutes instead of 1.3 minutes in order to take into account any possible incorporation problems.

Furthermore, the MMT group is conserved on the oligonucleotide for the purposes of subsequent purification. The oligonucleotide is finally deprotected in concentrated aqueous ammonia (16 h at 55° C.).

The reaction scheme is represented below.

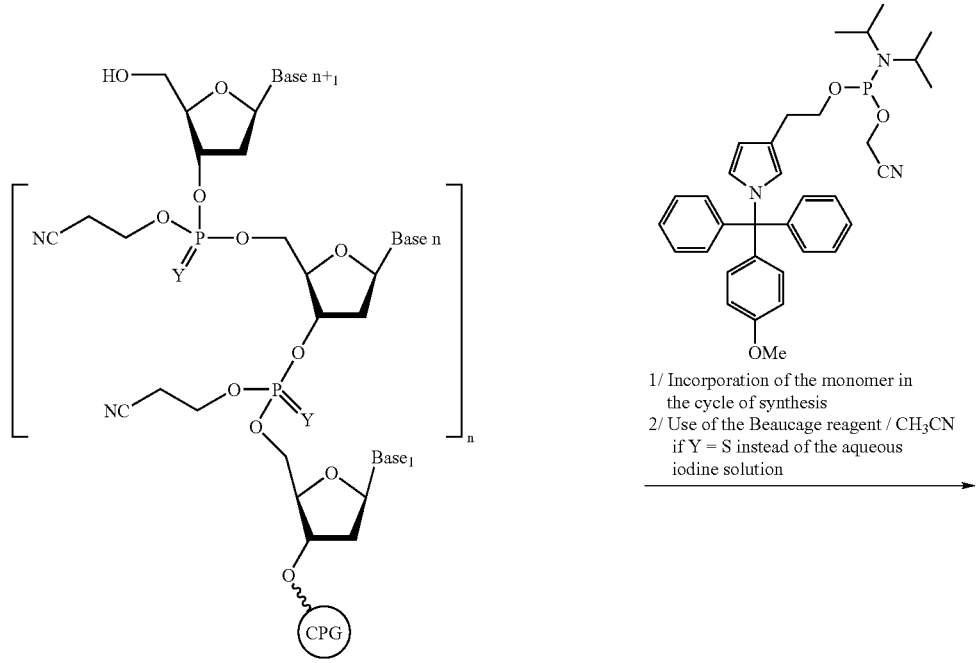

-continued
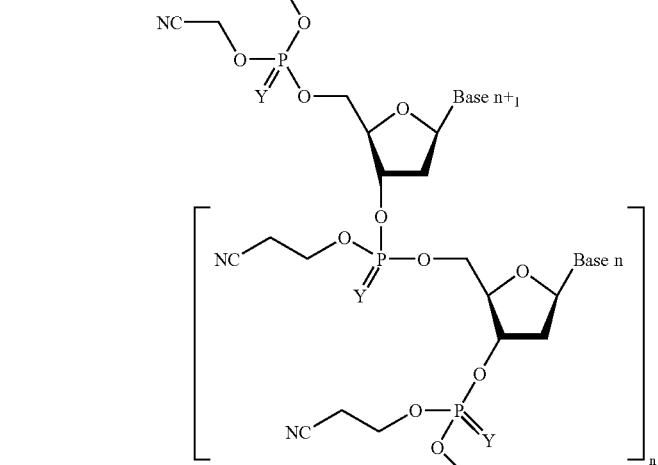
1/ 304 NH₃, 6 h, 55° C.
2/ AcON, 304 RT, 1 h
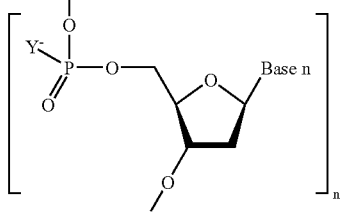
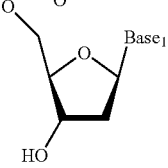
Y = O or S

Example 11

Cleavage of the Monomethoxytrityl Group and Purification of the Oligonucleotide The great advantage to using the monomethoxytritylated monomer is that it can be used for purifying the oligonucleotide and that it can be very readily eliminated in an acid medium. It will therefore be preferred compared with the tosyl group.

The oligonucleotide is purified by means of a manual purification system using the hydrophobic properties of the MMT group. (CTGen MDP—WS 1000™ column). This system is similar to the OPC™ cartridges (Applied Biosystems™) in which the oligonucleotide carrying the MMT group is specifically retained on the reverse phase, whereas the impurities that do not carry the MMT group are eluted in the liquid phase.

After elution of the abortive species, the oligonucleotide carrying the MMT was eluted with a solution of acetonitrile. After evaporation, the oligonucleotide was treated with an 80% acetic acid solution for one hour. The acid was evaporated off under cold conditions and the oligonucleotide was precipitated with ethanol. The purity of this compound was controlled by ion exchange chromatography on a Gen Pack Fax column (Waters) in an NaCl gradient (FIG. 3). FIG. 3 represents the purified oligonucleotide carrying the pyrrole substituted in the 3-position and synthesized from the monomer carrying MMT (gradient of 340 to 580 mM NaCl in 20 min, Gen Pack Fax™ column (Waters™), 0.75 ml/min).

Its purity is clearly greater than that which can be obtained with the tosylated monomer.

Example 12

Electrochemical Assembly

The manipulations were all carried out in an aqueous medium, using a three-electrode electrochemical assembly connected to an Autolab PGSTAT 100™ potentiostat. This imposes a fixed potential difference between the reference electrode and the working electrode, the counterelectrode serving to modulate the current so as to obtain the desired stable potential difference between the working electrode and the reference, whatever the electrical properties of the cell. Since the manipulations take place in an aqueous medium, the electrodes used were as follows: reference electrode=saturated Calomel electrode (SCE), counterelectrode=platinum wire, and working electrode=platinum disk 1 mm in diameter.

Example 13

Solutions Used (1) $LiClO_4$ Electrolyte in $H_2O$

Lithium perchlorate is the electrolyte used in the studied solutions. The product is in the form of a powder (molar mass 106.39 g·mol$^{-1}$) that is readily soluble in distilled water.
$LiClO_4$ electrolyte=0.5 M in $H_2O$.

(2) Solution for polymerization of 3-(hydroxyethyl)-pyrrole in the 3-(hydroxyethyl)pyrrole electrolyte=0.1 M
$LiClO_4$ electrolyte=0.5 M in $H_2O$ (3) Solution for copolymerization of 3-(hydroxyethyl)pyrrole with the pyrrole-ODN (oligonucleotide) in the 3-position The ODN (oligonucleotide) has the sequence:

5' GCCTTGACGATACAGCTA 3'   (SEQ ID NO: 3)

The pyrrole substituted with an oligonucleotide according to the invention (or pyrrole-ODN) is represented below:

(SEQ ID NO: 4)

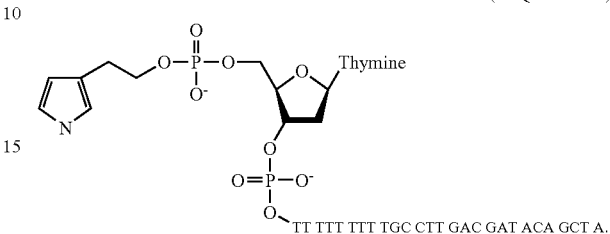

This solution was prepared with a ratio of 1 pyrrole-ODN unit per 20 000 pyrrole units.
3-(Hydroxyethyl)pyrrole=0.1 M
[Pyrrole-ODN]=5 μM
$LiClO_4$ electrolyte=0.5 M in $H_2O$.

(4) Solution for Polymerization of Pyrrole-ODN in the 3-position
[Pyrrole-ODN]=5 μM
$LiClO_4$ electrolyte=0.5 M in $H_2O$.

(5) 1× Hybridization Buffer HB

The 1×HB is the electrolyte medium used as hybridization solution. It has the following composition:
9.5 mM phosphate buffer,
0.515 M NaCl,
2.6 mM KCl,
0.048% Tween,
1× Denhardt's,
10 μg/ml salmon DNA.

(6) Solution for Hybridization of Noncomplementary Targets

A noncomplementary oligonucleotide of sequence, for example:
5' CGCCAGCAGCTCCAA 3' (SEQ ID NO: 5) was used at a concentration of 0.1 μM in 1×HB.

(7) Solution for Hybridization of Complementary Targets (CP)

An oligonucleotide complementary to the ODN immobilized in the polypyrrole film was used at a concentration of 0.1 μM in 1×HB.
5' TAGCTGTATCGTCAAGGC 3' (SEQ ID NO: 5).

Example 14

Principle of the Detection

The polymers according to the invention can in particular be used for detecting biologically active species that may be present in a sample and that are capable of reacting with the ODN present on the polymeric chain. Specifically, as shown hereinafter, it is observed that the conjugated polymers functionalized in the 3-position of their heterocycle exhibit, after reaction with one or more ligands, a modification of the electrochemical response compared with a reference polymer that has not reacted with the ligand(s) of a biological medium, visualized by means of a change in oxidation potential. This variation in the electrochemical signal of the polymer confers a sensor function and can thus be used to quantitatively measure the biologically active species, either by means of the variation in potential, at fixed current, or by means of the variation in current at fixed potential.

In the first part of the manipulations, it was verified that the monomers are polymerizable, the optimum polymerization parameters were established, and the conditions for stability and for electroactivity of the deposits in the solutions used were defined.

The essential point concerns the nature of the physicochemical properties of the polymer that are going to be modified during the "ODN/NA" (oligonucleotide/nucleic acid) recognition. In fact, in order to develop a method for rapid, sensitive and quantitative measurement of the presence of NA, the aim of the present invention concerns the development of materials that are electroactive in a single step, and the electrochemical response of which will be modified after "ODN/NA" hybridization. The modification will concern a variation of potentiometric type, by means of variation of the current for the oxidation potential of the polymer, or of amperometric type, by means of variation of the oxidation (or reduction) current observed at a given potential. These variations in electrochemical response may be measured quantitatively, the films of functionalized polymers being used as electrochemical sensors either of amperometric type or of potentiometric type.

Example 15

Modification of the Electrochemical Response Subsequent to Hybridization

A—Polymerization of the pyrroles-ODN in the 3-position on a polymeric prefilm of 3-(hydroxyethyl)pyrrole 1—Preparation of a polymeric prefilm of 3-(hydroxyethyl)pyrrole A current of 0.75 V is applied for 2.4 seconds (charges of 51 $mC \cdot cm^2$) using solution (2).

FIG. 4: First cycle of cyclic voltammetry for a 0.1M solution of 3-(hydroxyethyl)pyrrole monomers, on a platinum electrode (1 mm diameter) (0.5 M $LiClO_4$ electrolyte in $H_2O$, v=50 $mV \cdot s^{-1}$).

FIG. 5: Cyclic voltammetry curve for an electrode modified with a polymeric film of 3-(hydroxyethyl)-pyrrole transferred into the electrolyte free of monomer.

(0.5 M $LiClO_4$ in $H_2O$, v=50 $mV \cdot s^{-1}$)

It was assumed that this polymer makes the surface homogeneous and serves as anchoring points for initiating the second layer of polymerization of pyrroles substituted in the 3-position with ODNs. Currently, it is not possible to perform a hompolymerization of pyrroles substituted in the 3-position with ODNs, directly on the electrode. Thus, the polymerization of pyrrole-ODNs alone on this polymeric prefilm would make it possible to increase the amount of ODN probes immobilized on the support and therefore to observe a more obvious modification of the electrochemical response of the polymer.

2—The Polymerization of the Pyrrole-ODN in the 3-position on the Prefilm is Carried Out at 0.6 V for 115 Seconds (Charges of 19 $mC \cdot cm^{-2}$) Using Solution (4)

FIG. 6: First cycle of cyclic voltammetry in a 5 μM solution of pyrrole-ODN in the 3-position, on a platinum electrode (1 mm diameter) (0.5 M $LiClO_4$ electrolyte in $H_2O$), v=50 $mV \cdot s^{-1}$.

The transfer of the double-layer polymer into the $LiClO_4$ electrolyte solution is presented in the cyclic voltammetry FIG. 7:

Cycles in 0.5 M $LiClO_4$ in $H_2O$, (a) for the polymeric sublayer of 3-(hydroxyethyl)pyrrole (Q=57 $mC \cdot cm^{-2}$), (b) for the sublayer and the polypyrrole-ODN in the 3-position (Q=15 $mC \cdot cm^{-2}$), v=50 $mV \cdot s^{-1}$.

The deposit is transferred into the hybridization buffer (solution (5)), then brought into the presence of noncomplementary targets (solution (6)), rinsed, and then brought into the presence of complementary targets (solution (7)).

In these various solutions, the deposit is analyzed (cycled) by cyclic voltammetry.

The results obtained are given in FIG. 8, which shows a decrease in electroactivity of the oxidation peak and also a shift in potential of the oxidation peak.

FIG. 8: Modification of the electrochemical signal of the modified electrode subjected to various solutions. Cycles in 1×HB, v=50 $mV \cdot s^{-1}$. a: 3 days in 1×HB; b: 1 h in M5; c: 2 h in CP.

The pyrrole-ODN in the 3-position polymer is therefore capable of translating the phenomenon of hybridization of these probes into an electrochemical signal.

B—Copolymerization of 3-(hydroxyethyl)pyrrole/pyrrole-ODN in the 3-position, on a polymeric prefilm of 3-(hydroxyethyl)pyrrole 1—Preparation of a polymeric prefilm of 3-(hydroxyethyl)pyrrole A current of 0.75 V is applied for 0.5 seconds (charges of 9 $mC \cdot cm^{-2}$) using solution (2).

2—The copolymerization of 3-(hydroxyethyl)-pyrrole/pyrrole-ODN in the 3-position, on the prefilm, is carried out at 0.75 V for 1.3 seconds (charges of 30 $mC \cdot cm^{-2}$) using solution (3)

FIG. 9: Cyclic voltammetry curves of the film containing two layers of the polymers in 0.5 M $LiClO_4$ in $H_2O$; (a) for the polymeric sublayer of 3-(hydroxyethyl)pyrrole (Q=37 $mC \cdot cm^{-2}$), (b) for the sublayer and copolymer substituted in the 3-position (Q=60 $mC \cdot cm^{-2}$), v=50 $mV \cdot s^{-1}$.

The deposit is transferred into the hybridization buffer (solution (5)), then brought into the presence of noncomplementary targets (solution (6)), rinsed, and then brought into the presence of complementary targets (solution (7)).

In these various solutions, the deposit is analyzed (cycled) by cyclic voltammetry.

The results obtained are shown in FIG. 10, which shows a decrease in electroactivity of the oxidation peak and also a slight shift in potential of the oxidation peak.

FIG. 10: Modification of the electrochemical signal of the modified electrode subjected to a: Hybridization buffer b: Hybridization solution in the presence of noncomplementary targets c: Hybridization solution in the presence of complementary targets.

The copolymer 3-(hydroxyethyl)pyrrole/pyrrole-ODN in the 3-position is therefore capable of translating the phenomenon of hybridization of these probes into an electrochemical signal.

C—Direct copolymerization of 3-(hydroxyethyl)pyrrole with pyrrole-ODN in the 3-position, directly on the platinum electrode Solution for copolymerization of 3-(hydroxyethyl)-pyrrole with the pyrrole-ODN in the 3-position This solution was prepared with a ratio of 1 pyrrole-ODN unit per 20 000 pyrrole units.

3-(Hydroxyethyl)pyrrole=0.1 M.
[Pyrrole-ODN]=5 μM.
$LiClO_4$ electrolyte=0.5 M in $H_2O$.

The copolymerization takes place at 0.75 V on a platinum electrode 3 mm in diameter, platinum counter-electrode, SCE reference, agitation and degassing under argon for 15 min before deposition, deposition time 20 s, charge obtained=7.39 mC.

The deposit produced is subsequently transferred into an electrolyte solution and into the hybridization buffer. The appearance of the cyclic voltammetry curve confirms the presence of an electroactive film that is stable and reversible.

Modification of the electrochemical signal of the modified electrode subjected to a: cyclic voltammetry in the hybridization buffer at 20 mV/s,
b: cyclic voltammetry in the hybridization buffer at 20 mV/s in the presence of the noncomplementary probes after 20 min,
c: cyclic voltammetry in the hybridization buffer at 20 mV/s in the presence of the complementary probes, t=5 min,
d: cyclic voltammetry in the hybridization buffer at 20 mV/s in the presence of the complementary probes after 20 min.

The addition of noncomplementary targets shows a slight shift in potential of 10 mV.

The presence of complementary targets results in a displacement of approximately 60 mV after 20 min.

The invention claimed is:

1. A pyrrole substituted with an oligonucleotide corresponding to general formula (I):

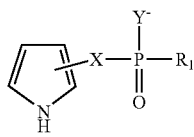

where:
$R_1$ represents an oligonucleotide,
Y represents S or O,
X represents a spacer arm chosen from $-(CH_2)_n-O-$, $-(CH_2)_p-O-[(CH_2)_2-O]_q-$, $-(CH_2)_r-CO-NR'-(CH_2)_{r'}-O-$, $-(CH_2)_r-NCH_3-(CH_2)_{r'}-O-$, $-(CH_2)_r-CO-NR'-[(CH_2)_2-O]_s-$, $-(CH_2)_r-NCH_3-[(CH_2)_2-O]_s-$,
R' represents $-H$ or $-CH_3$,
n is an integer from 1 to 5,
p is an integer from 1 to 2,
q is an integer from 1 to 4,
r is an integer from 1 to 3,
r' is an integer from 1 to 3,
s is an integer from 1 to 3,
n, p, q, r, r' and s are identical or different, and
the pyrrole ring is substituted in the 2-, 3-, 4- or 5-position.

2. The pyrrole substituted with an oligonucleotide as claimed in claim 1, corresponding to general formula (II):

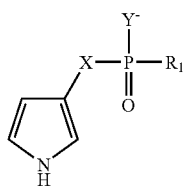

where:
$R_1$ represents an oligonucleotide;
Y represents S or O;
X represents a spacer arm chosen from $-(CH_2)_n-O-$, $-(CH_2)_p-O-[(CH_2)_2-O]_q-$, $-(CH_2)_r-CO-NR'-(CH_2)_{r'}-O-$, $-(CH_2)_r-NCH_3-(CH_2)_{r'}-O-$, $-(CH_2)_r-CO-NR'-[(CH_2)_2-O]_s-$, $-(CH_2)_r-NCH_3-[(CH_2)_2-O]_s-$;
R' represents $-H$ or $-CH_3$;
n is an integer from 1 to 5;
p is an integer from 1 to 2;
q is an integer from 1 to 4;
r is an integer from 1 to 3;
r' is an integer from 1 to 3;
s is an integer from 1 to 3;
n, p, q, r, r' and s are identical or different.

3. The pyrrole substituted with an oligonucleotide as claimed in claim 2, wherein X is $-(CH_2)_n-O-$ and n is equal to 2.

4. The pyrrole substituted with an oligonucleotide as claimed in claim 1, corresponding to general formula (III):

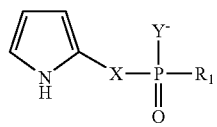

where:
$R_1$ represents an oligonucleotide;
Y represents S or O;
X represents a spacer arm chosen from $-(CH_2)_n-O-$, $-(CH_2)_p-O-[(CH_2)_2-O]_q-$, $-(CH_2)_r-CO-NR'-(CH_2)_{r'}-O-$, $-(CH_2)_r-NCH_3-(CH_2)_{r'}-O-$, $-(CH_2)_r-CO-NR'-[(CH_2)_2-O]_s-$, $-(CH_2)_r-NCH_3-[(CH_2)_2-O]_s-$;
R' represents $-H$ or $-CH_3$;
n is an integer from 1 to 5;
p is an integer from 1 to 2;
q is an integer from 1 to 4;
r is an integer from 1 to 3;
r' is an integer from 1 to 3;
s is an integer from 1 to 3; and
n, p, q, r, r' and s are identical or different.

5. The pyrrole substituted with an oligonucleotide as claimed in claim 4, wherein X is $-(CH_2)_n-O-$ and n is equal to 2.

6. A method for preparing a conductive electroactive copolymer functionalized with oligonucleotides, comprising:
a) providing at least one monomer selected from the pyrroles substituted with an oligonucleotide as claimed in claim 2, b) providing at least one monomer selected from substituted pyrroles capable of polymerizing with other pyrroles,
c) electrochemically copolymerizing the monomer of step a) with the monomer of step b).

7. The method for preparing a conductive electroactive copolymer functionalized with oligonucleotides as claimed in claim 6, wherein the molar ratio of the substituted pyrrole of step a) to the substituted pyrrole of step b) is from 1/1000 to 1/100 000.

8. A method for preparing a conductive electroactive copolymer functionalized with oligonucleotides, comprising:
   a) providing at least one monomer chosen from substituted pyrroles capable of polymerizing with other pyrroles,
   b) electrochemically polymerizing the monomer of step a) to form a first conductive electroactive polymer,
   c) providing a monomer selected from the pyrroles substituted with an oligonucleotide as claimed in claim 2,
   d) providing at least one monomer selected from substituted pyrroles capable of polymerizing with other pyrroles,
   e) electrochemically copolymerizing the monomer of step c) with the monomer of step d) on said first conductive electroactive polymer formed in step b), so as to obtain a conductive electroactive copolymer functionalized with oligonucleotides.

9. The method for preparing a conductive electroactive copolymer functionalized with oligonucleotides as claimed in claim 8, wherein the molar ratio of the substituted pyrrole of step c) to the substituted pyrrole of step d) is from 1/1000 to 1/100 000.

10. A method for preparing a conductive electroactive copolymer functionalized with oligonucleotides, comprising:
    a) providing at least one monomer selected from substituted pyrroles capable of polymerizing with other pyrroles,
    b) electrochemically polymerizing the monomer of step a) to form a first conductive electroactive polymer,
    c) providing a monomer selected from the pyrroles substituted with an oligonucleotide as claimed in claim 2,
    d) electrochemically polymerizing the monomer of step c) on said first conductive electroactive polymer formed in step b), to obtain a conductive electroactive polymer functionalized with oligonucleotides.

11. A method for preparing a conductive electroactive copolymer functionalized with oligonucleotides, comprising:
    a) providing at least one monomer selected from the substituted pyrroles capable of polymerizing with other pyrroles is provided,
    b) electrochemically polymerizing the monomer of step a) to form a first conductive electroactive polymer,
    c) providing a pyrrole substituted with an oligonucleotide as claimed in claim 4,
    d) electrochemically coupling the substituted pyrrole of step c) on said first conductive electroactive polymer formed in step b) to obtain a conductive electroactive copolymer functionalized with oligonucleotides.

12. A conductive electroactive copolymer functionalized with oligonucleotides, obtained by the method as claimed in claim 6.

13. An electrode, comprising a conductive support surface-coated with at least one conductive electroactive copolymer functionalized with oligonucleotides as claimed in claim 12.

14. A matrix of electrodes, comprising at least one electrode as claimed in claim 13.

15. A device for detecting an analyte in a sample, comprising at least one copolymer as claimed in claim 12.

16. A device for detecting an analyte in a sample, comprising at least one matrix of electrodes as claimed in claim 14.

17. A method for detecting an analyte in a sample, comprising:
    a) providing a conductive electroactive copolymer functionalized with oligonucleotides as claimed in claim 12;
    b) contacting said electroactive copolymer of step a) with the sample under reaction conditions that are suitable for a specific interaction of the analyte with said oligonucleotides;
    c) detecting the analyte attached to said oligonucleotides an electrical measurement.

18. The method as claimed in claim 17, wherein in step c), a DNA or an RNA that hybridizes specifically to said oligonucleotides of the conductive electroactive copolymer is detected.

19. The method as claimed in claim 17, wherein in step c), a variation in potential or a variation in current is measured.

20. A method for preparing a pyrrole substituted with an oligonucleotide of claim 1, comprising:
    a) cycles for synthesizing an oligonucleotide are carried out,
    b) in the final cycle for synthesizing said oligonucleotide, a substituted pyrrole of general formula (IV)

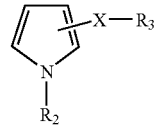

where:
   $R_2$ is an amine-protecting group chosen from monomethoxytrityl, dimethoxytrityl, tosyl, triisopropylsilyl, tert-butoxycarbonyl, 9-fluorenyloxycarbonyl, benzyloxycarbonyl and acetyl,
   $R_3$ is a phosphorus-comprising group capable of reacting with a free hydroxyl group, chosen from a phosphotriester, H-phosphonate or phosphoramidite group,
   X represents a spacer arm chosen from —$(CH_2)_n$—O—, —$(CH_2)_p$—O—[$(CH_2)_2$—O$]_q$—, —$(CH_2)_r$—CO—NR'—$(CH_2)_r$—O—, —$(CH_2)_r$—NCH$_3$—$(CH_2)_r$—O—, —$(CH_2)_r$—CO—NR'—[$(CH_2)_2$—O$]_s$—, —$(CH_2)_r$—NCH$_3$—[$(CH_2)_2$—O$]_s$—,
   R' represents —H or —$CH_3$;
   n is an integer from 1 to 5,
   p is an integer from 1 to 2,
   q is an integer from 1 to 4,
   r is an integer from 1 to 3,
   r' is an integer from 1 to 3,
   s is an integer from 1 to 3,
   n, p, q, r, r' and s are identical or different, and
   the pyrrole ring is substituted in the 2-, 3-, 4- or 5-position, is substituted at the final nucleotide in the 5' position or in the 3' position of said oligonucleotide; and
   c) said amine-protecting group $R_2$ is cleaved.

21. The method as claimed in claim 20, wherein, in step b), the protective group $R_2$ is monomethoxytrityl and in step c), the protective group is cleaved by treatment in an acid medium.

* * * * *

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: embodiment of oligonucleotide to be
      pyrrole-substituted

<400> SEQUENCE: 1
tttttttttt tgccttgacg atacagcta                                    29

<210> SEQ ID NO 2
<211> LENGTH: 22
<212> TYPE: DNA
<213> ORGANISM: Artificial Sequence
<220> FEATURE:
<223> OTHER INFORMATION: embodiment of oligonucleotide to be
      pyrrole-substituted

<400> SEQUENCE: 2
atctcgggaa tctcaatgtt ag                                           22

<210> SEQ ID NO 3
<211> LENGTH: 18
<212> TYPE: DNA
<213> ORGANISM: Artificial Sequence
<220> FEATURE:
<223> OTHER INFORMATION: embodiment of oligonucleotide to be
      pyrrole-substituted

<400> SEQUENCE: 3
gccttgacga tacagcta                                                18

<210> SEQ ID NO 4
<211> LENGTH: 28
<212> TYPE: DNA
<213> ORGANISM: Artificial Sequence
<220> FEATURE:
<223> OTHER INFORMATION: embodiment of oligonucleotide to be
      pyrrole-substituted with linker polynucleotide

<400> SEQUENCE: 4
tttttttttt gccttgacga tacagcta                                     28

<210> SEQ ID NO 5
<211> LENGTH: 15
<212> TYPE: DNA
```

```
<213> ORGANISM: Artificial Sequence
<220> FEATURE:
<223> OTHER INFORMATION: embodiment of non-complementary oligonucleotide

<400> SEQUENCE: 5
cgccagcagc tccaa                                                    15

<210> SEQ ID NO 6
<211> LENGTH: 18
<212> TYPE: DNA
<213> ORGANISM: Artificial Sequence
<220> FEATURE:
<223> OTHER INFORMATION: embodiment of complementary oligonucleotide

<400> SEQUENCE: 6
tagctgtatc gtcaaggc                                                 18
```